(12) United States Patent
Holcomb et al.

(10) Patent No.: US 8,469,252 B2
(45) Date of Patent: Jun. 25, 2013

(54) SURGICAL STAPLER FASTENING DEVICE WITH ADJUSTABLE ANVIL

(75) Inventors: Matthew D. Holcomb, Lebanon, OH (US); Jason L. Harris, Mason, OH (US); Michael J. Stokes, Cincinnati, OH (US); Mark S. Zeiner, Mason, OH (US); Jonathan B. O'Keefe, North Attleboro, MA (US); Keith D. Boudreau, Beverly, MA (US); Jeffrey C. Cerier, Franklin, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 181 days.

(21) Appl. No.: 13/015,966

(22) Filed: Jan. 28, 2011

(65) Prior Publication Data

US 2012/0125971 A1 May 24, 2012

Related U.S. Application Data

(63) Continuation-in-part of application No. 12/690,311, filed on Jan. 20, 2010, now abandoned, and a continuation-in-part of application No. 12/608,860, filed on Oct. 29, 2009, and a continuation-in-part of application No. 12/609,336, filed on Oct. 30, 2009, and a continuation-in-part of application No. 12/359,351, filed on Jan. 26, 2009, and a continuation-in-part of application No. 12/359,354, filed on Jan. 26, 2009, and a continuation-in-part of application No. 12/359,357, filed on Jan. 26, 2009.

(51) Int. Cl.
*A61B 17/068* (2006.01)

(52) U.S. Cl.
USPC .................. 227/175.1; 227/19; 227/179.1

(58) Field of Classification Search
USPC ....................... 227/175.1, 19, 179.1
See application file for complete search history.

(56) References Cited

U.S. PATENT DOCUMENTS

| 2,185,518 | A | 1/1940 | Posnack |
| 3,638,847 | A | 2/1972 | Noiles et al. |
| 3,740,994 | A | 6/1973 | DeCarlo, Jr. |

(Continued)

FOREIGN PATENT DOCUMENTS

| EP | 0068046 B1 | 5/1988 |
| EP | 0864297 B1 | 6/2007 |

(Continued)

OTHER PUBLICATIONS

Talebpour M, Amoli BS. Laparoscopic total gastric vertical plication in morbid obesity. J Laparoendosc Adv Surg Tech A 2007;17:793-8.

(Continued)

*Primary Examiner* — Brian D Nash

(57) ABSTRACT

A fastener applying device including a staple housing having a proximal end attached to a handle, a distal end, and a longitudinal axis therebetween. There is at least one fastener within the housing. The device also includes an anvil movable within the staple housing. The anvil has a proximal position and a distal position, wherein when in the distal position a distal end of the anvil extends distal to the distal end of the staple housing by a distance. The device also includes an adjustment nut connecting the staple housing to the handle. Rotation of the adjustment nut changes the distance.

1 Claim, 30 Drawing Sheets

U.S. PATENT DOCUMENTS

| | | | |
|---|---|---|---|
| 3,819,100 A | | 6/1974 | Noiles et al. |
| 4,086,926 A | | 5/1978 | Green et al. |
| 4,289,133 A | * | 9/1981 | Rothfuss .................... 227/175.3 |
| 4,331,276 A | * | 5/1982 | Bourque .......................... 227/8 |
| 4,396,139 A | | 8/1983 | Hall et al. |
| 4,407,286 A | | 10/1983 | Noiles et al. |
| 4,456,161 A | * | 6/1984 | Russell ........................... 227/67 |
| 4,489,875 A | | 12/1984 | Crawford et al. |
| 4,505,273 A | | 3/1985 | Braun et al. |
| 4,509,518 A | | 4/1985 | McGarry et al. |
| 4,624,254 A | | 11/1986 | McGarry et al. |
| 4,648,542 A | | 3/1987 | Fox et al. |
| 4,669,647 A | | 6/1987 | Storace |
| 4,700,703 A | * | 10/1987 | Resnick et al. ............. 227/176.1 |
| 4,874,122 A | | 10/1989 | Froelich et al. |
| 4,899,745 A | | 2/1990 | Laboureau et al. |
| 5,156,609 A | | 10/1992 | Nakao et al. |
| 5,312,023 A | * | 5/1994 | Green et al. ................. 227/175.1 |
| 5,312,024 A | * | 5/1994 | Grant et al. ................. 227/179.1 |
| 5,333,772 A | | 8/1994 | Rothfuss et al. |
| 5,350,400 A | | 9/1994 | Esposito et al. |
| 5,392,978 A | | 2/1995 | Velez et al. |
| 5,413,584 A | | 5/1995 | Schulze |
| 5,439,468 A | | 8/1995 | Schulze et al. |
| 5,465,894 A | * | 11/1995 | Clark et al. ................. 227/175.1 |
| 5,465,895 A | * | 11/1995 | Knodel et al. ............... 227/176.1 |
| 5,484,095 A | * | 1/1996 | Green et al. ................. 227/181.1 |
| 5,544,802 A | | 8/1996 | Crainich |
| 5,564,615 A | * | 10/1996 | Bishop et al. ............... 227/175.1 |
| 5,626,585 A | | 5/1997 | Mittelstadt et al. |
| 5,630,540 A | * | 5/1997 | Blewett ........................ 227/176.1 |
| 5,645,567 A | | 7/1997 | Crainich |
| 5,692,668 A | * | 12/1997 | Schulze et al. ............. 227/175.1 |
| 5,715,987 A | | 2/1998 | Kelley et al. |
| 5,725,554 A | | 3/1998 | Simon et al. |
| 5,732,871 A | | 3/1998 | Clark et al. |
| 5,762,255 A | * | 6/1998 | Chrisman et al. ........... 227/175.2 |
| 5,829,662 A | * | 11/1998 | Allen et al. ................. 227/177.1 |
| 6,228,098 B1 | | 5/2001 | Kayan et al. |
| 6,269,997 B1 | * | 8/2001 | Balazs et al. ............... 227/175.1 |
| 6,277,131 B1 | | 8/2001 | Kalikow |
| 6,306,149 B1 | | 10/2001 | Meade |
| 6,330,964 B1 | | 12/2001 | Kayan et al. |
| 6,352,541 B1 | | 3/2002 | Kienzle et al. |
| 6,450,391 B1 | | 9/2002 | Kayan et al. |
| 6,453,780 B2 | * | 9/2002 | Habermehl ..................... 81/434 |
| 6,530,933 B1 | | 3/2003 | Yeung et al. |
| 6,695,854 B1 | | 2/2004 | Kayan et al. |
| 6,767,356 B2 | | 7/2004 | Kanner et al. |
| 6,837,895 B2 | | 1/2005 | Mayenberger |
| 6,915,937 B2 | | 7/2005 | Lat et al. |
| 6,957,756 B2 | | 10/2005 | Lat et al. |
| 7,056,330 B2 | | 6/2006 | Gayton |
| 7,059,331 B2 | * | 6/2006 | Adams et al. .................. 128/898 |
| 7,059,509 B2 | | 6/2006 | Brown |
| 7,112,214 B2 | | 9/2006 | Peterson et al. |
| 7,179,265 B2 | | 2/2007 | Manetakis et al. |
| 7,320,692 B1 | | 1/2008 | Bender et al. |
| 7,344,544 B2 | | 3/2008 | Bender et al. |
| 7,407,076 B2 | * | 8/2008 | Racenet et al. .............. 227/175.1 |
| 7,458,978 B1 | | 12/2008 | Bender et al. |
| 7,473,258 B2 | | 1/2009 | Clauson et al. |
| 7,506,791 B2 | * | 3/2009 | Omaits et al. ............... 227/177.1 |
| 7,533,790 B1 | | 5/2009 | Knodel et al. |
| 7,753,870 B2 | | 7/2010 | Demarais et al. |
| 7,832,408 B2 | * | 11/2010 | Shelton et al. ................. 128/898 |
| 2004/0225305 A1 | | 11/2004 | Ewers et al. |
| 2005/0080454 A1 | | 4/2005 | Drews et al. |
| 2005/0085830 A1 | | 4/2005 | Lehman et al. |
| 2005/0116009 A1 | * | 6/2005 | Milliman .................... 227/176.1 |
| 2006/0020276 A1 | | 1/2006 | Saadat et al. |
| 2006/0060630 A1 | * | 3/2006 | Shelton et al. .............. 227/175.2 |
| 2007/0185504 A1 | | 8/2007 | Manetakis et al. |
| 2008/0045598 A1 | | 2/2008 | Brueggemeier et al. |
| 2008/0078805 A1 | * | 4/2008 | Omaits et al. .............. 227/176.1 |
| 2008/0082124 A1 | * | 4/2008 | Hess et al. ..................... 606/219 |
| 2008/0249566 A1 | | 10/2008 | Harris et al. |
| 2008/0314957 A1 | * | 12/2008 | Boudreaux ................. 227/175.2 |
| 2008/0319455 A1 | | 12/2008 | Harris et al. |
| 2009/0072006 A1 | | 3/2009 | Clauson et al. |
| 2009/0112233 A1 | | 4/2009 | Xiao |
| 2009/0112304 A1 | * | 4/2009 | Weadock et al. ............. 623/1.11 |
| 2009/0134198 A1 | | 5/2009 | Knodel et al. |
| 2009/0134199 A1 | * | 5/2009 | Heinrich et al. ........... 227/178.1 |
| 2009/0206127 A1 | | 8/2009 | Danielson et al. |
| 2009/0318936 A1 | | 12/2009 | Harris et al. |
| 2010/0187283 A1 | | 7/2010 | Crainich et al. |
| 2010/0187284 A1 | * | 7/2010 | Crainich et al. ........... 227/176.1 |
| 2010/0191255 A1 | | 7/2010 | Crainich et al. |
| 2010/0237132 A1 | * | 9/2010 | Measamer et al. ......... 227/180.1 |

FOREIGN PATENT DOCUMENTS

| | | |
|---|---|---|
| EP | 1908423 B1 | 1/2011 |
| WO | WO 01/76489 A1 | 10/2001 |
| WO | WO 2008/109876 A1 | 9/2008 |
| WO | WO 2008/112942 A2 | 9/2008 |
| WO | WO 2008/118928 A2 | 10/2008 |
| WO | WO 2009/137517 A1 | 11/2009 |
| WO | WO 2012103286 A1 | 8/2012 |
| WO | WO 2012103291 A1 | 8/2012 |

OTHER PUBLICATIONS

Sales Puccini, CE. Surset gástrico de Sales: una alternative para cirugia bariátrica restrictive. Rev Colomb Cir 2008;23(3):131-5.

Fusco PEB, Poggetti RS, Younes RN, Fontes B, Birolini D. Evaluation of gastric greater curvature invagination for weight loss in rats. Obes Surg 2006;16:171-7.

Fusco PEB, Poggetti RS, Younes RN, Fontes B, Birolini D. Comparison of anterior gastric wall and greater gastric curvature invaginations for weight loss in rats. Obes Surg 2007;17:1340-5.

Ramos AC, Galvao M, Behrens E, Montufar F, Zundel N. Tubular sleeve gastroplasty (TSG) as a new approach to bariatric treatment. 14th World Congress of the International Federation for the Surgery of Obesity—Paris, France—Aug. 26-29, 2009.

Brethauer SA, Harris JL, Chand B, Kroh M, Rogula T, Schauer PR. Initial results of vertical gastric plication for severe obesity. Society of American Gastrointestinal and Endoscopic Surgeons. Phoenix, Arizona. Apr. 22-25, 2009.

International Search Report dated Jun. 1, 2010 (PCT/US2010/021929).

International Search Report dated Aug. 13, 2010 (PCT/US2010/021953).

International Search Report dated Apr. 7, 2011 (PCT/US2011/020472).

International Search Report dated Apr. 10, 2012 (PCT/US2012/022656).

International Search Report dated Apr. 10, 2012 (PCT/US2012/022651).

European Search Report, dated Oct. 1, 2012, Application No. 12172811.7.

European Search Report, dated Oct. 1, 2012, Application No. 12172808.3.

European Search Report, dated Oct. 1, 2012, Application No. 12172816.6.

Co-pending U.S. Appl. No. 12/359,351, filed Jan. 26, 2009, first named inventor Jason L. Harris.

Co-pending U.S. Appl. No. 12/359,354, filed Jan. 26, 2009, first named inventor Jason L. Harris.

Co-pending U.S. Appl. No. 12/359,357, filed Jan. 26, 2009, first named inventor Jason L. Harris.

Co-pending U.S. Appl. No. 12/608,860, filed Oct. 29, 2009, first named inventor Jason L. Harris.

Co-pending U.S. Appl. No. 12/609,336, filed Oct. 30, 2009, first named inventor Jason L. Harris.

Co-pending U.S. Appl. No. 12/690,285, filed Jan. 20, 2010, first named inventor Lawrence Crainich.

Co-pending U.S. Appl. No. 13/015,977, filed Jan. 28, 2011, first named inventor Jason L. Harris.

Co-pending U.S. Appl. No. 13/164,949, filed Jun. 21, 2011, first named inventor Matthew D. Holcomb.

Co-pending U.S. Appl. No. 13/164,954, filed Jun. 21, 2011, first named inventor Matthew D. Holcomb.

Co-pending U.S. Appl. No. 13/164,960, filed Jun. 21, 2011, first named inventor Jason L. Harris.
Co-pending U.S. Appl. No. 13/164,963, filed Jun. 21, 2011, first named inventor Jason L. Harris.
Co-pending U.S. Appl. No. 13/362,172, filed Jan. 31, 2012, first named inventor Jason L. Harris.
Co-pending U.S. Appl. No. 13/371,678, filed Feb. 13, 2012, first named inventor Jason L. Harris.
Co-pending U.S. Appl. No. 13/371,684, filed Feb. 13, 2012, first named inventor Jason L. Harris.

\* cited by examiner

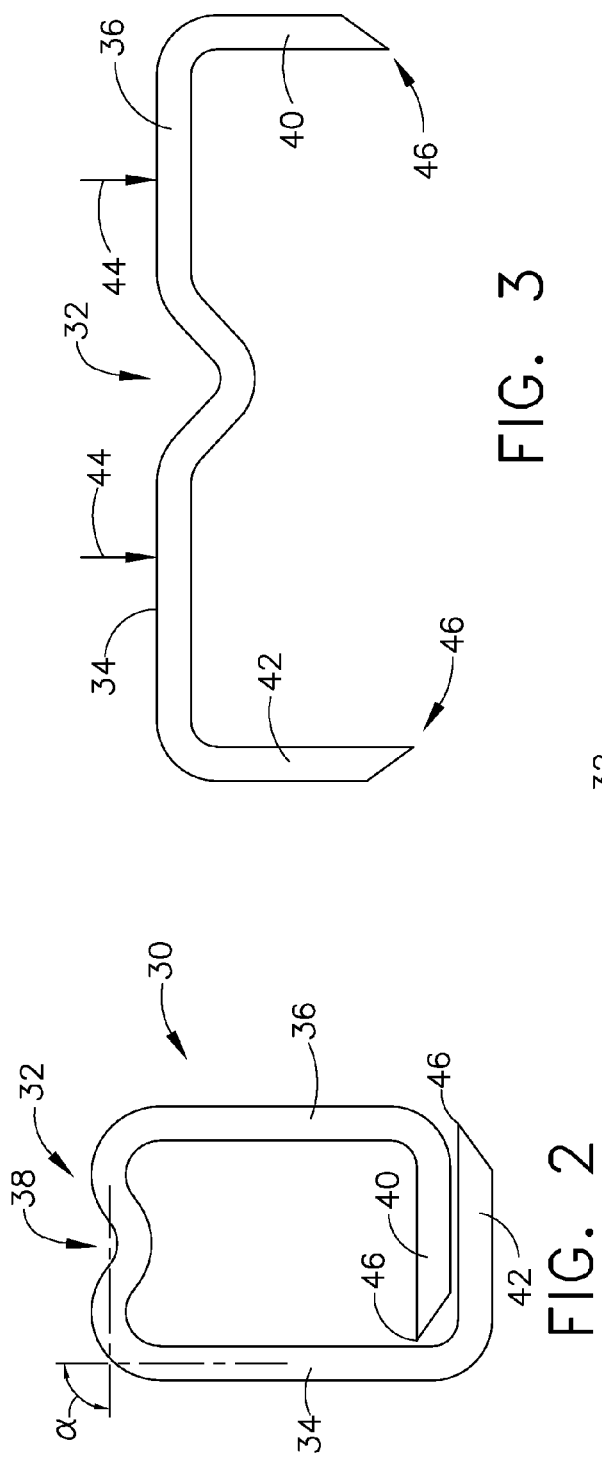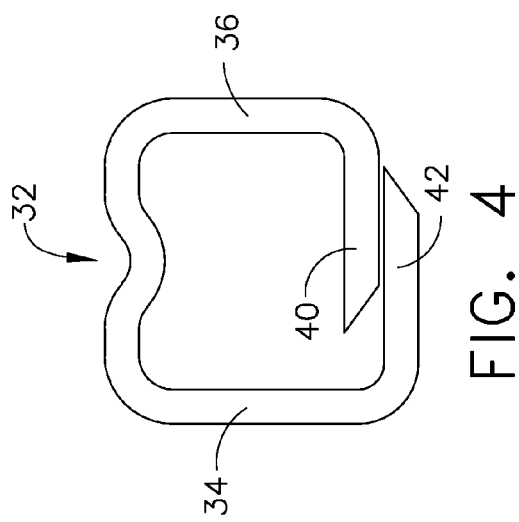

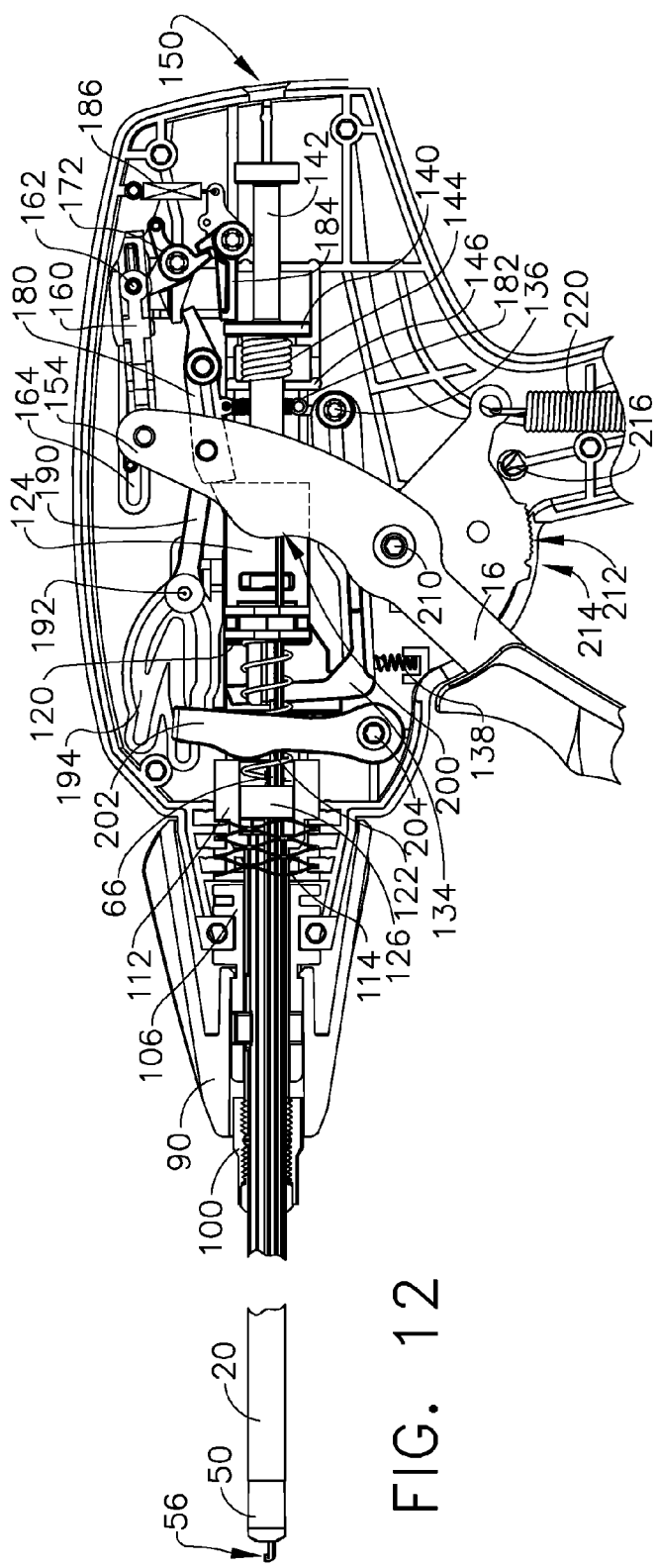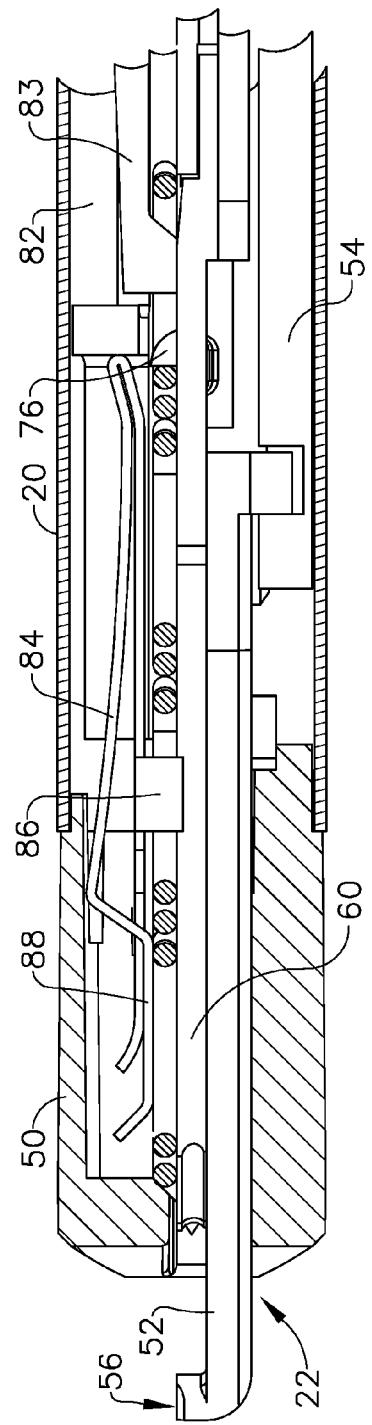

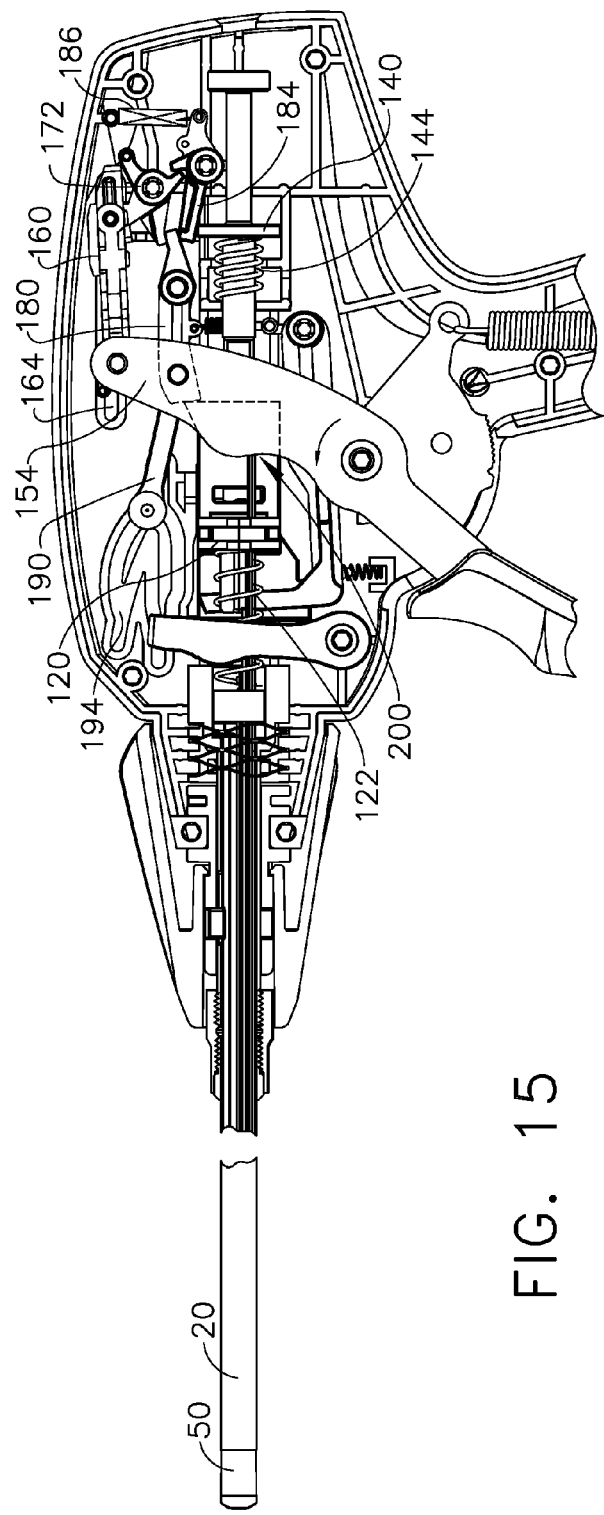
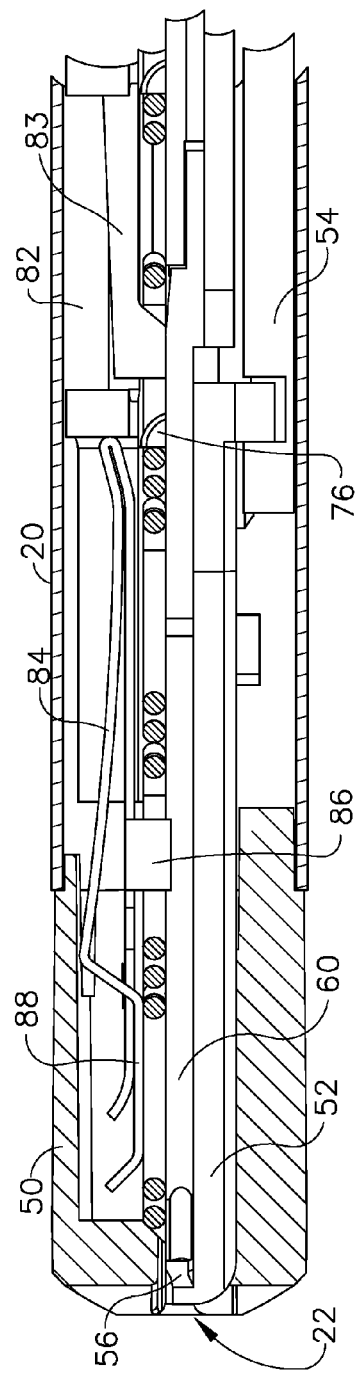
FIG. 15
FIG. 16

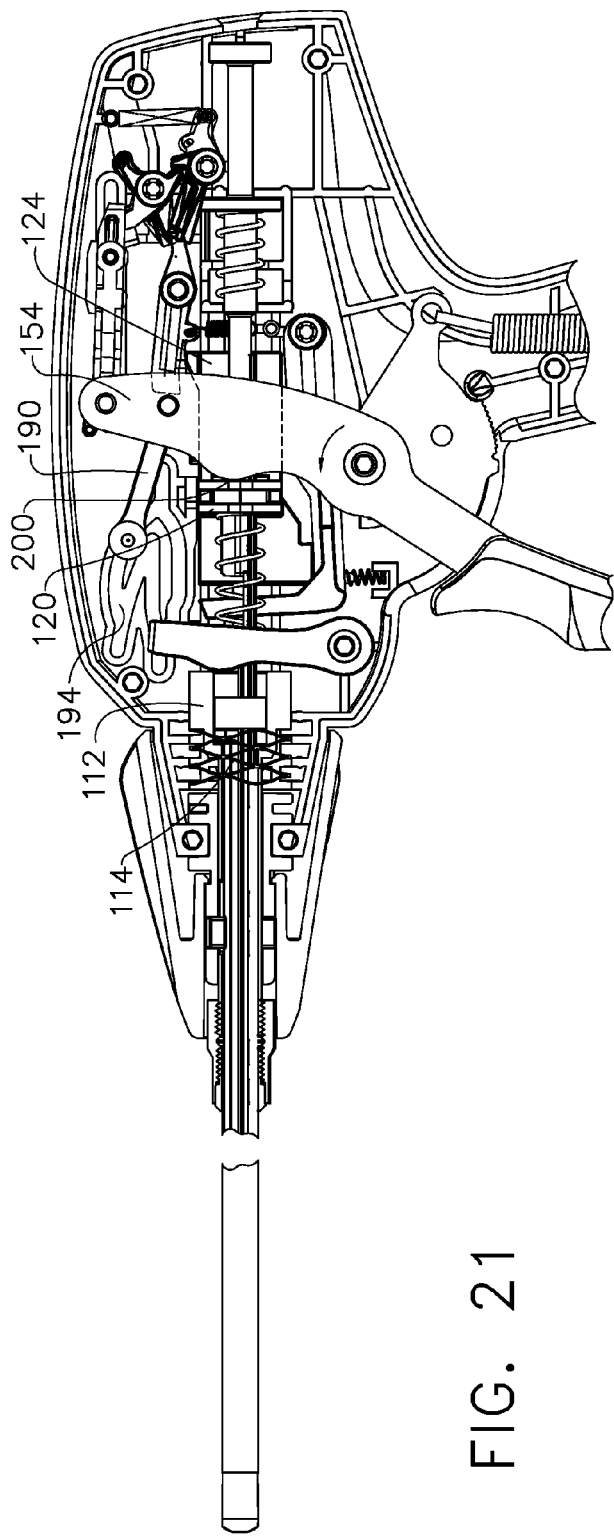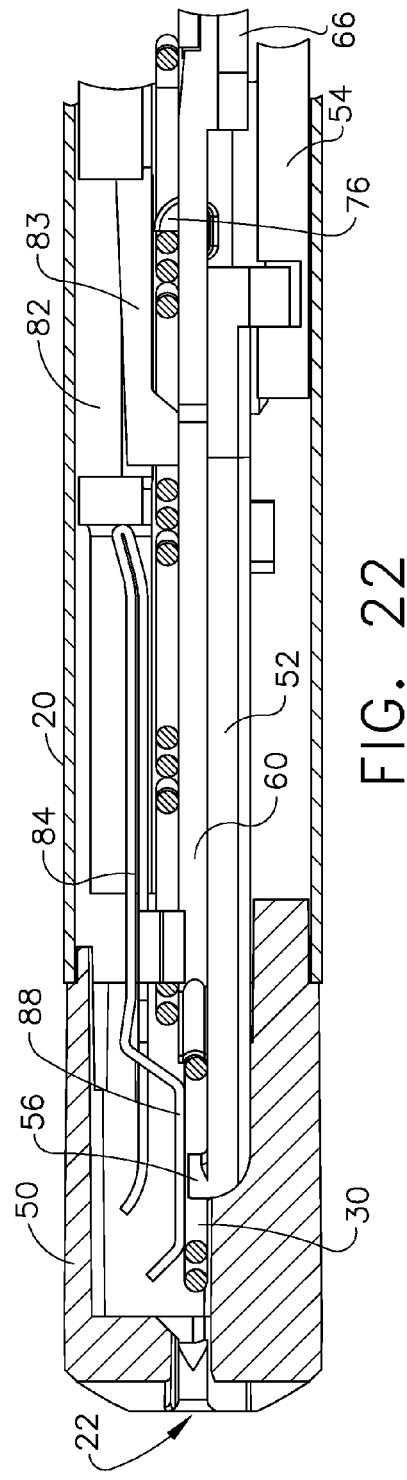

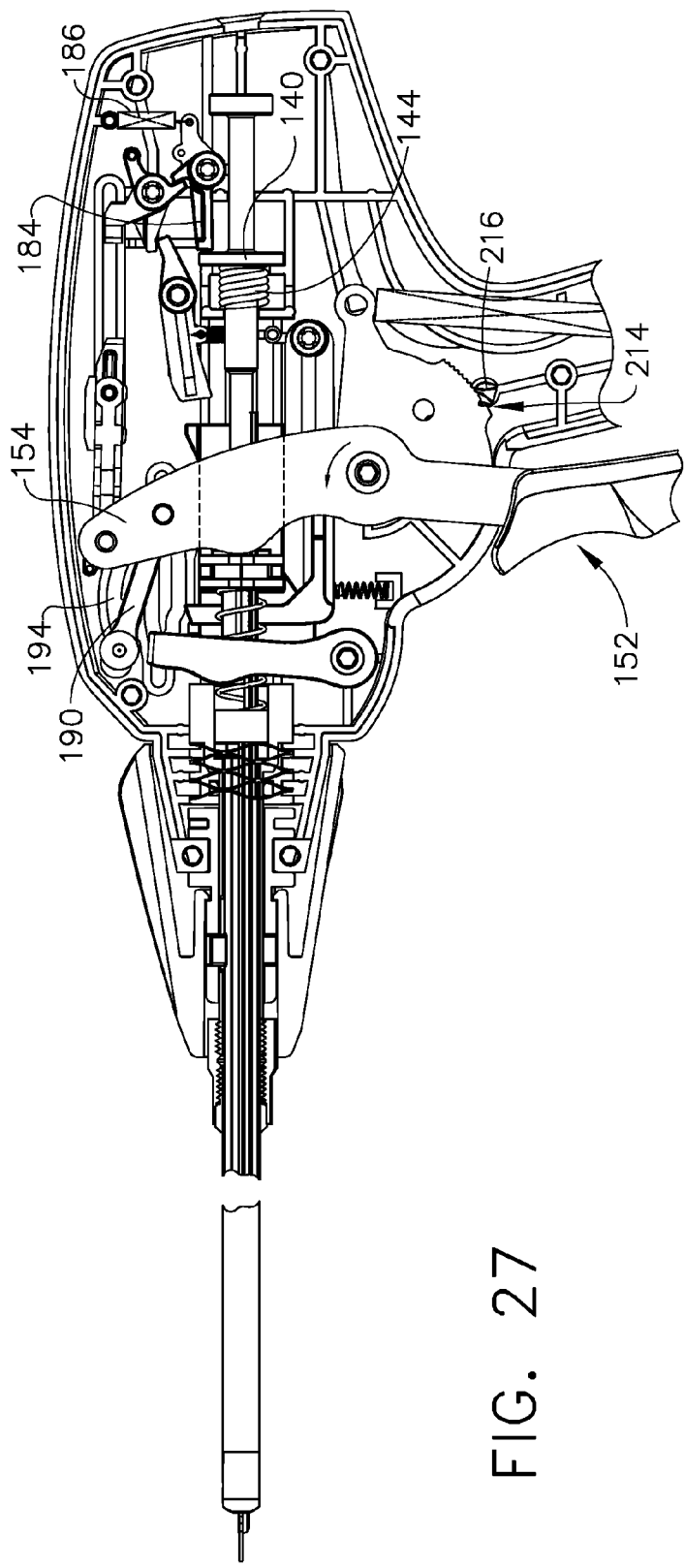
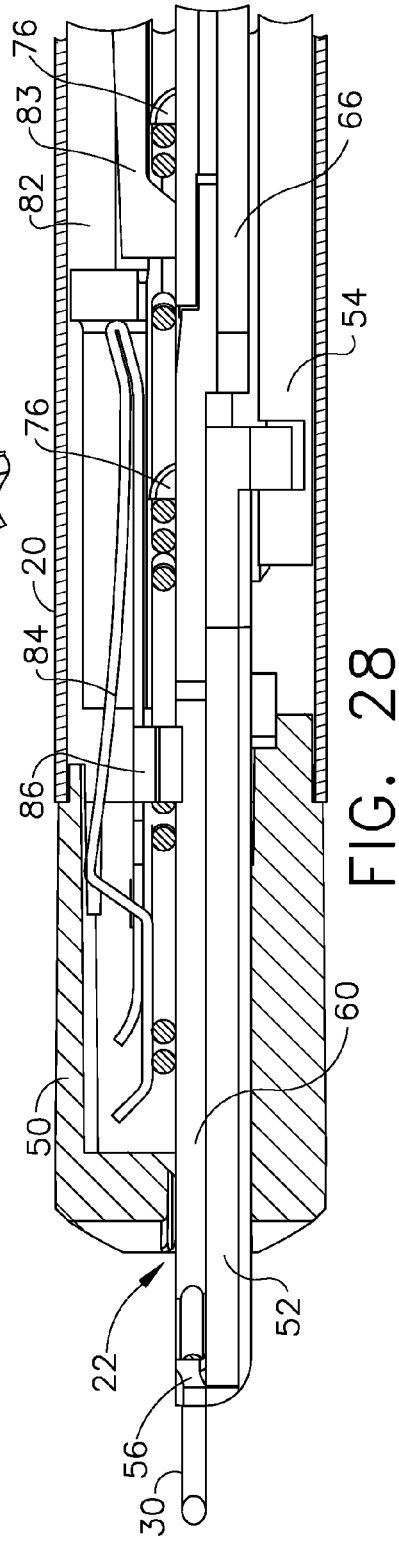
FIG. 27
FIG. 28

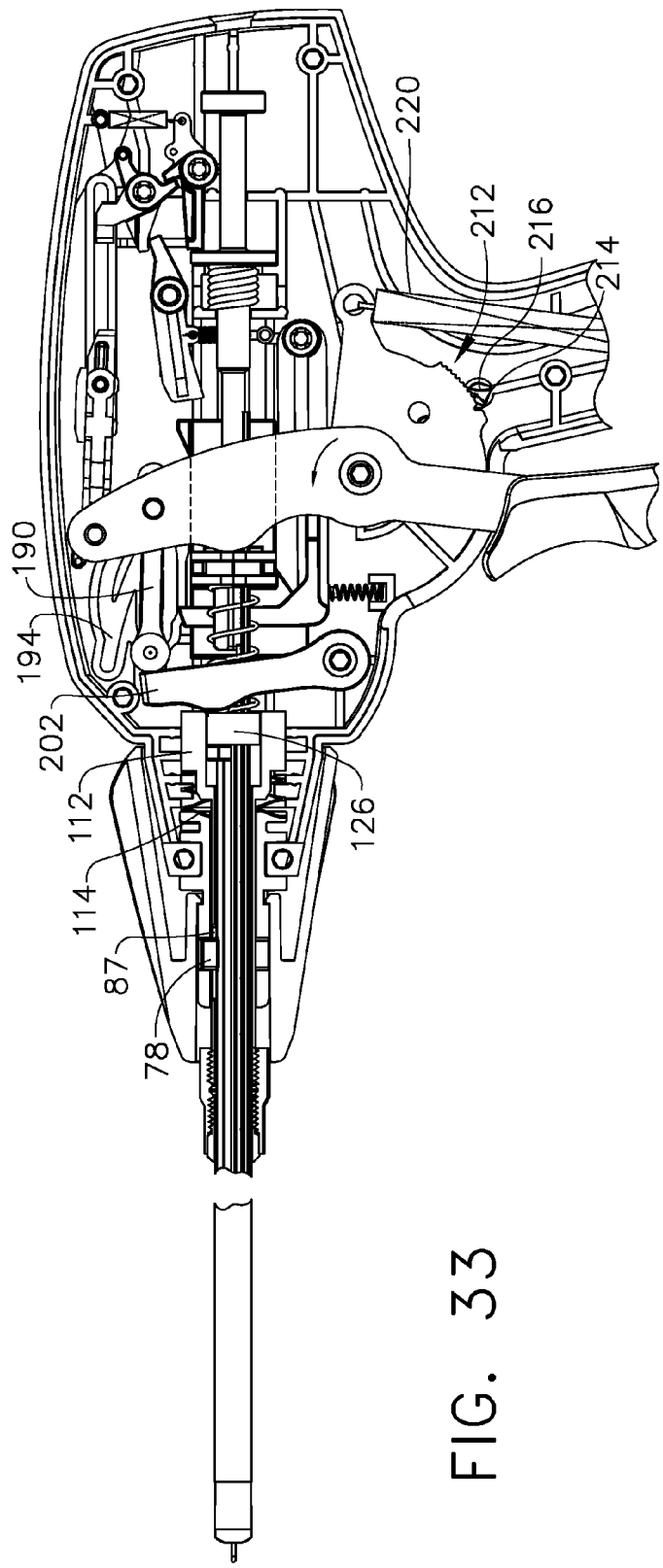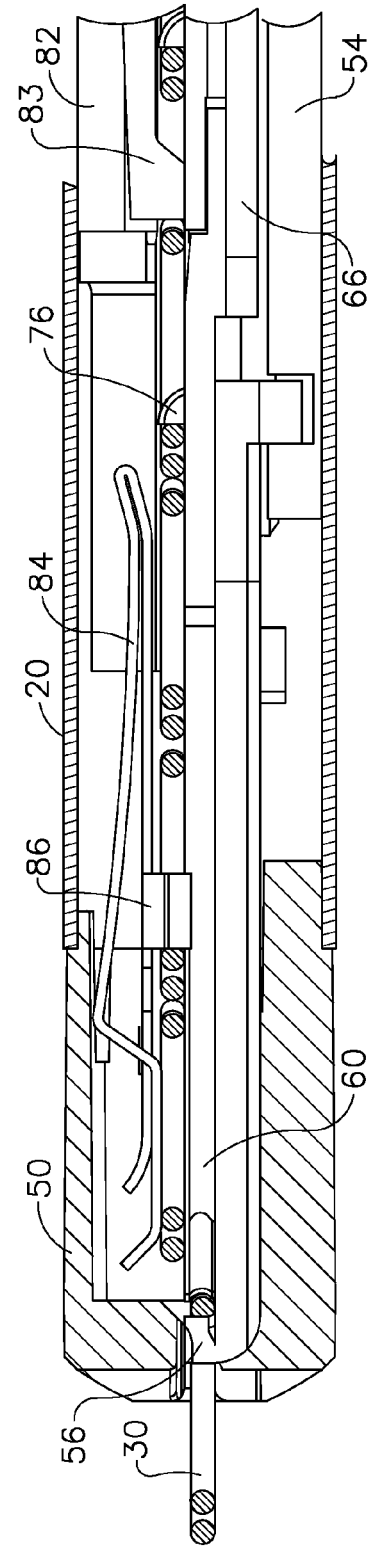

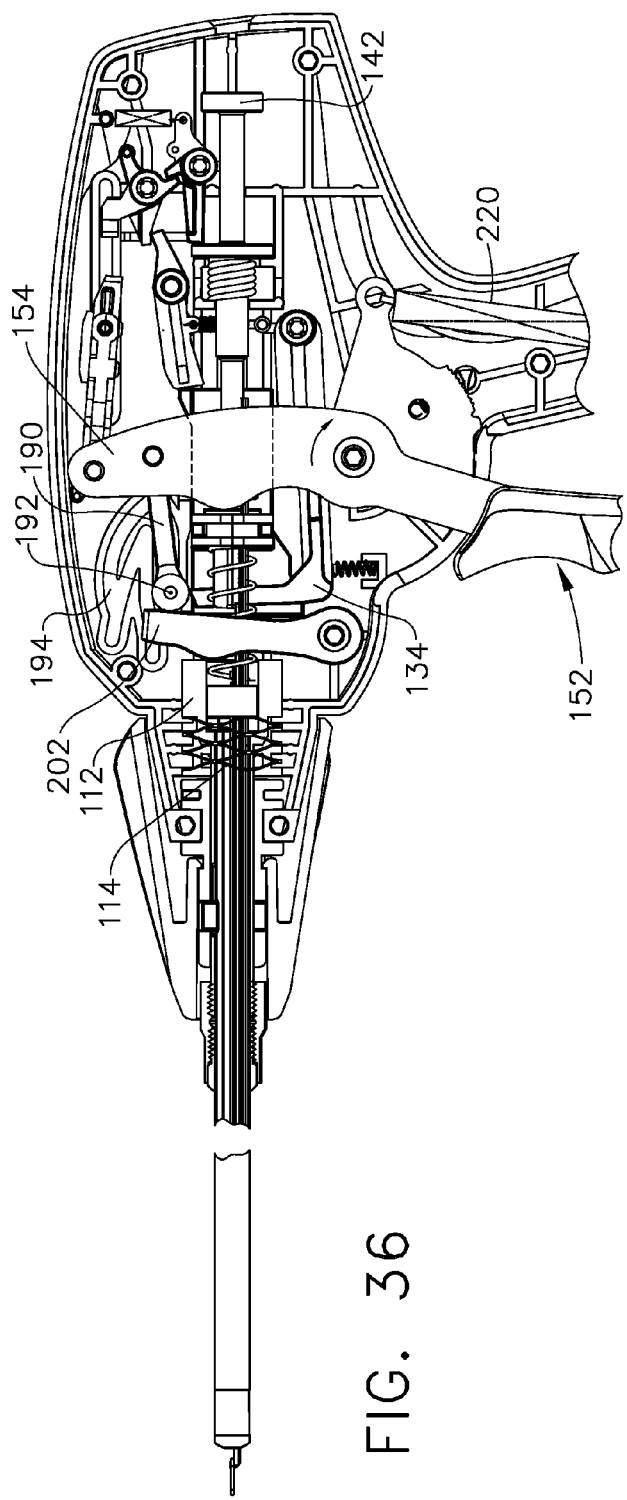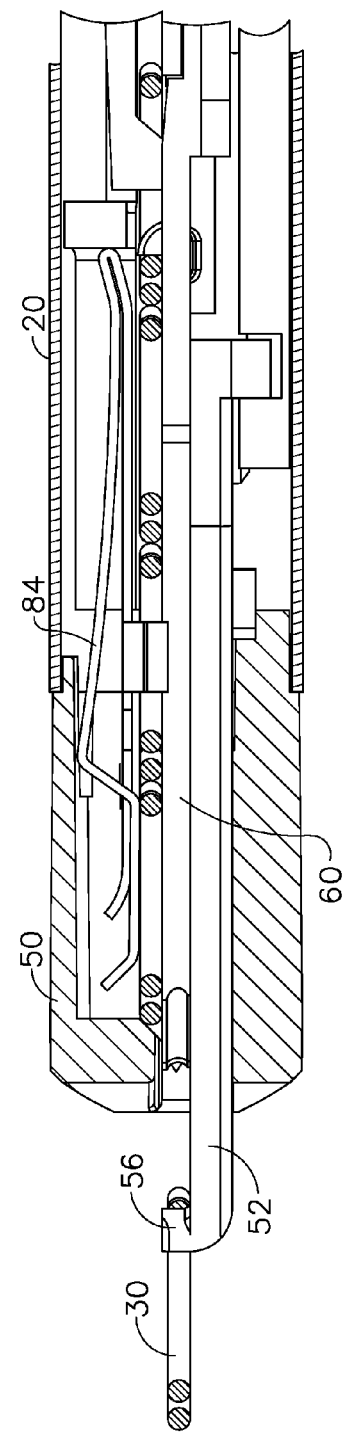
FIG. 36
FIG. 37

SURGICAL STAPLER FASTENING DEVICE WITH ADJUSTABLE ANVIL

REFERENCE TO RELATED APPLICATIONS

This application is a continuation-in-part of U.S. Pending application Ser. No. 12/690,311 filed on Jan. 20, 2010 now abandoned; and is a is a continuation-in-part of U.S. patent application Ser. No. 12/608,860 filed Oct. 29, 2009; and is a continuation-in-part of U.S. patent application Ser. No. 12/609,336 filed Oct. 30, 2009; and is a continuation-in-part of U.S. patent application Ser. No. 12/359,351 filed Jan. 26, 2009; and is a continuation-in-part of U.S. patent application Ser. No. 12/359,354 filed Jan. 26, 2009; and is a continuation-in-part of U.S. patent application Ser. No. 12/359,357 filed Jan. 26, 2009.

FIELD OF THE INVENTION

The present invention relates in general to the joining of cavity wall tissue with a surgical stapler and, more particularly, to a low profile stapler for delivering multiple large-sized box staples to a body cavity through a small delivery port. The low profile stapler enables large areas of tissue to be joined together inside a body cavity through a small access port.

BACKGROUND OF THE INVENTION

Obesity is a medical condition affecting more than 30% of the population in the United States. Obesity affects an individual's quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m2 and obesity as a BMI of 30 kg/m2. Morbid obesity is defined as BMI 40 kg/m2 or being 100 lbs. overweight. Obesity and its co-morbidities are estimated to cost an excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone may be ineffective for reducing excess body weight in many patients.

A surgical procedure has been developed for involuting the gastric cavity wall to reduce stomach volume as a treatment for obesity. In the gastric volume reduction (GVR) procedure (e.g., reduction gastroplasty, gastric plication, greater curvature plication, anterior surface plication, etc.), multiple pairs of suture anchoring devices, such as T-Tag anchors, are deployed through the gastric cavity wall. Preferably, the suture anchors are deployed through a small diameter port in a minimally invasive surgical procedure to reduce trauma to the patient. Following deployment of the T-Tag anchors, the suture attached to each individual pair of anchors is cinched to approximate the tissue and secured to involute the cavity wall between the anchors. This procedure is described in greater detail in co-pending U.S. patent application Ser. Nos. 11/779,314, 11/779,322, 12/113,829, 12/179,600, 12/359,351, 12/609,336, and 12/690,311, which are hereby incorporated herein by reference in their entirety. Procedure variations of particular interest include the case where the involution occurs about the midline of the anterior surface of the stomach, the case where the involution occurs about the greater curvature of the stomach following the removal or relaxing of attachment points along the greater curve (e.g., dissection of the short gastric vessels, dissection of the omentum from the gastric wall, etc.), and combinations of these (e.g., the involution begins near the gastro-esophageal junction and extends about the greater curve and transitions to the anterior surface near the incisura angularis). Preclinical outcomes around fastener durability for gastric plication procedures in a canine model are discussed in Menchaca et al. "Gastric plication: preclinical study of durability of serosa-to-serosa apposition". *Surg Obes Relat Dis* 2011; 7:8-14. Clinical outcomes discussing different gastric plication procedures are discussed in Brethauer et al. "Laparoscopic gastric plication for the treatment of severe obesity". *Surg Obes Relat Dis* 2011; 7:15-22. One effect of the procedure is to more rapidly induce feelings of satiation defined herein as achieving a level of fullness during a meal that helps regulate the amount of food consumed. Another effect of this procedure is to prolong the effect of satiety which is defined herein as delaying the onset of hunger after a meal which in turn regulates the frequency of eating. By way of a non-limiting list of examples, positive impacts on satiation and satiety may be achieved by a GVR procedure through one or more of the following mechanisms: reduction of stomach capacity, rapid engagement of stretch receptors, alterations in gastric motility, pressure induced alteration in gut hormone levels, and alterations to the flow of food either into or out of the stomach. As an example, a stomach with a reduced capacity will distend more quickly for a given volume of food. This distension of the stomach may trigger stretch receptors which in turn trigger a sense of satiation. In another example, the procedure will limit the stomach's ability to expand, effectively reducing its capacity or fill volume. Additionally, the procedure may induce a beneficial hormonal effect due either to the more rapid triggering of stretch receptors in certain regions of the stomach or the prevention of hormone release by eliminating triggering mechanisms from being engaged in the infolded region that no longer experiences stretch in the same manner. In yet another example, the procedure may alter gastric emptying by preventing efficient antral contractions. Additionally, the infolded region may provide a restrictive inlet into the stomach just distal to the esophagogastric junction. The GVR procedures described in these applications require individual placement of each suture anchor pair into the cavity wall tissue, and subsequent tensioning of the suture between the anchor pairs in order to involute the tissue. This individual placement of the T-Tag anchors and manual suture tensioning is time intensive; increasing the duration, complexity and cost of the GVR procedure. Accordingly, it is desirable to have a simpler, faster, and less expensive means for forming a tissue fold within the peritoneal cavity.

It is known to use surgical staples for binding and holding body tissues together following an anastomosis, skin closure, or other surgical procedure. Traditionally, these staples have had a wide U-shape in the undeformed state, requiring a large incision site or wide diameter trocar cannula to accommodate the staples and stapler. Staples and staplers having a lower profile have been developed for use in smaller diameter (i.e. 5 mm or 10 mm) trocars. However, these devices suffer from a number of deficiencies which make them impractical for use in the GVR procedure. In particular, such staplers require bending the staple a full 180° from the predeployment, stacked condition in the stapler to the closed, deployed condition in the tissue. Obtaining this degree of plastic deformation requires that the staple be composed of a soft, ductile material, such as soft titanium. However, the use of a soft ductile material decreases the strength and holding power of the formed staple, thus making the staple unsuitable for the pressures associated with involuting the gastric cavity wall without an impractical number of staples. Staples having a triangular prefiring configuration have also been developed for deployment through a low profile stapler. However, the triangular shape of these staples prevents the staples from being stacked and fed longitudinally through the stapler shaft. Instead, the staples are stacked and fed vertically within the stapler, which reduces the number of staples that can be deployed from the stapler while still maintaining a low profile diameter. Since some versions of the GVR procedure may require a large number of staples to involute the cavity wall, vertical stacking would necessitate using more than one stapler to complete a procedure. Additionally, previous staplers have bent staples at three or fewer points during formation and deployment, which reduces the amount of work hardening and, thus, strengthening within the formed staple.

Accordingly, to facilitate GVR and other surgical procedures, it is desirable to have an improved surgical staple and deploying stapler for fastening layers of tissue within the peritoneal cavity. It is desirable that the stapler has a low profile for use through a small diameter laparoscopic port, a single trocar containing multiple small laparoscopic ports, or through a semi-rigid or flexible endoscopic platform (e.g., for use in natural orifice surgical procedures), yet be capable of deploying staples with a large tissue purchase. Further, it is desirable that the staples have a folded, box shape, and that a large quantity of the staples be deliverable by a single stapler during a procedure. Additionally, it is desirable to have a stapler which alters the configuration of a staple from a low profile, reduced width prior to deployment to a wider, operable width following deployment. The present invention provides a surgical staple and stapler which achieves these objectives.

BRIEF DESCRIPTION OF THE DRAWINGS

FIG. 2 is a top view of an exemplary staple embodiment shown in an initial, undeployed condition;

FIG. 3 is a top view of the staple of FIG. 2 shown in an intermediate deployment condition;

FIG. 4 is a top view of the staple of FIG. 2 shown in a final, deployed condition;

FIG. 12 is a side, partially sectional view of the distal end and handle of the stapler showing an initial deployment condition;

FIG. 13 is a side, partially sectional view of the distal end of the stapler showing the staple deploying assembly in an initial deployment condition;

FIG. 15 is a side, partially sectional view of the distal end and handle of the stapler showing the actuator lobes pivoted distally to release the anvil latch;

FIG. 16 is a side, partially sectional view showing the distal end of the stapler in the same deployment condition as FIG. 15, with the anvil retracted proximally against the clamp;

FIG. 21 is a side, partially sectional view of the distal end and handle of the stapler showing a deployment condition in which the actuator advances the clamp distally;

FIG. 22 is a side, partially sectional view showing the distal end of the stapler in the same deployment condition as FIG. 21, with the clamp contacting the back span of a staged staple;

FIG. 27 is a side, partially sectional view of the distal end and handle of the stapler showing a deployment condition in which the clamp and anvil are locked in a fully distal position;

FIG. 28 is a side, partially sectional view showing the distal end of the stapler in the same deployment condition as FIG. 27, with the fully distal clamp and anvil opening the staple outside the distal deployment opening;

FIG. 33 is a side, partially sectional view of the distal end and handle of the stapler showing a deployment condition in which the actuator is re-closing and pushing the former distally;

FIG. 34 is a side, partially sectional view showing the distal end of the stapler in the same deployment condition as FIG. 33, with the former advancing to close the staple outside the distal deployment opening;

FIG. 36 is a side, partially sectional view of the distal end and handle of the stapler showing a deployment condition in which the actuator pivots open to draw the former and clamp back proximally from the closed staple;

FIG. 37 is a side, partially sectional view showing the distal end of the stapler in the same deployment condition as FIG. 36, with the clamp and former drawn back proximally from the closed staple.

DETAILED DESCRIPTION OF THE INVENTION

Figure 1:
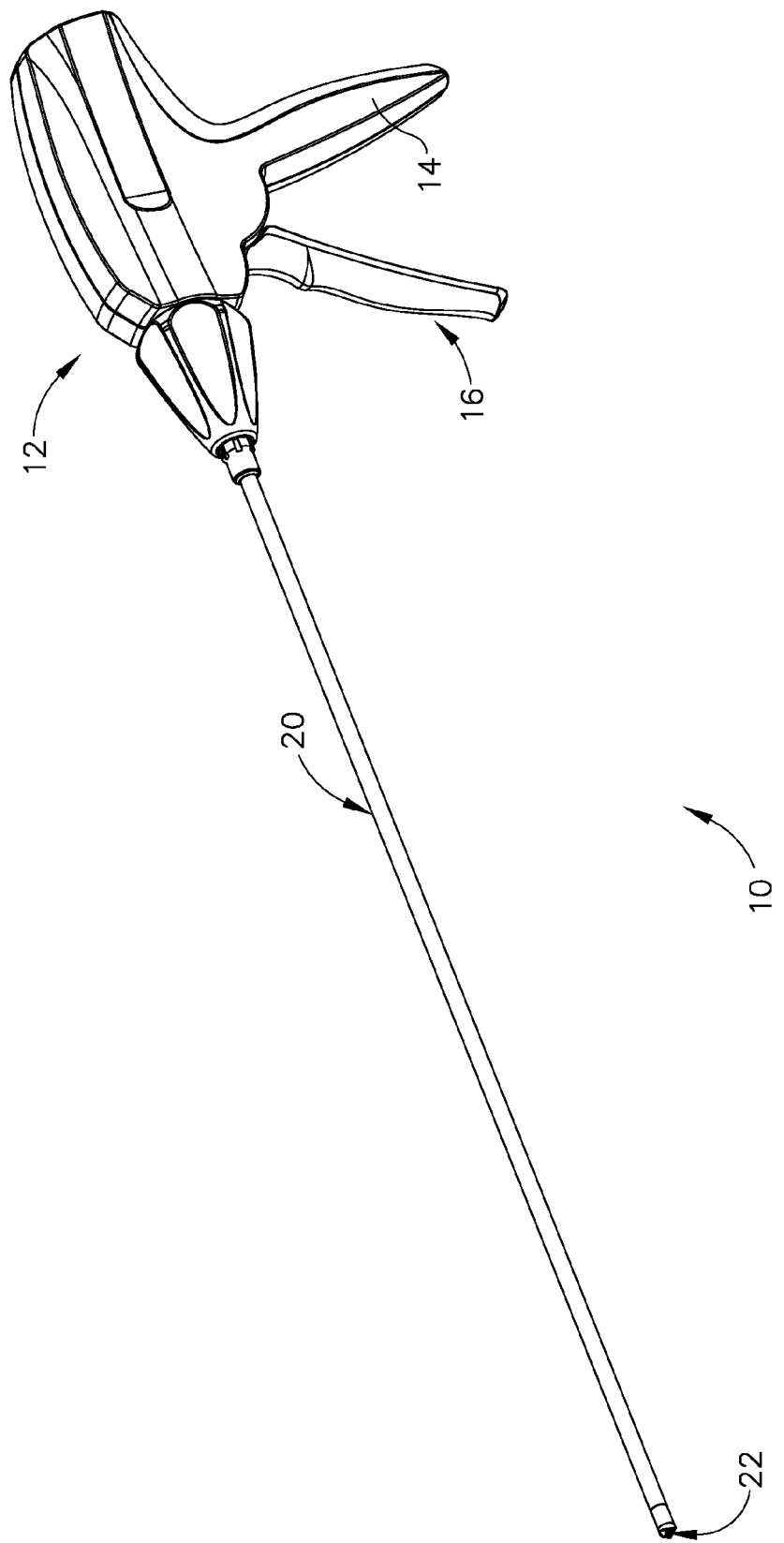
FIG. 1 is an isometric view of an exemplary low profile surgical stapler of the present invention.

Referring now to the drawing figures, in which like numerals indicate like elements throughout the views, FIG. 1 illustrates an exemplary low profile surgical stapler for use in GVR and other small incision site procedures in the peritoneal cavity including, but not limited to, reinforcement of staple lines (e.g., "oversewing" of a vertical sleeve gastrectomy), closing of surgical defects (e.g., gastrotomy closure), and fixation of temporary (e.g., liver retraction) or permanent (e.g., hernia mesh, gastric band securement) medical devices. As shown in FIG. 1, the stapler 10 includes a handle 12 having a pistol grip 14 shaped for grasping by a surgeon. An actuator 16 is movably coupled to handle 12 to be drawn towards the pistol grip 14 during staple deployment. An elongated staple housing 20 having a longitudinal axis extends distally from handle 12. Housing 20 has sufficient length (on the order of 18") to enable use within an obese patient at numerous trocar access sites for traditional laparoscopic approaches. Likewise, housing 20 is sized to allow for passage through a small (3-5 mm) diameter trocar, although functional devices of a larger diameter are also possible without departing from the overall scope of the invention. A staple deploying assembly is at least partially disposed within the interior of housing 20 for discharging staples from a distal deployment opening 22. Staples are individually advanced outside of the open stapler end 22, and expanded open through actuation of the handle. After the staple pierces or otherwise engages the tissue sections to be joined, the stapler draws the expanded staple legs back inward to close the staple through the tissue.

To obtain a large tissue purchase (which is desirable in GVR procedures) while using a small diameter delivery shaft, stapler 10 deploys fasteners or staples having a folded, closed loop configuration. These closed loop or "box" staples have a small width in the initial, unformed condition. The width of the staple is expanded during opening and forming to allow the staple to obtain a large tissue purchase. FIG. 2 illustrates an exemplary box staple 30 for deployment from stapler 10. Staple 30 comprises a length of wire formed into a crown or back span 32 and first and second leg portions 34, 36 that intersect with opposite ends of the back span. The wire has a cylindrical cross-section, but may have other shapes (e.g., rectangular, elliptical, etc.) to provide optimal strength for the application or to aid in the feeding of the staples, and may or may not be uniform along the length of the wire. Leg portions 34, 36 intersect with back span 32 at an approximate angle α of 90° and extend in a substantially parallel fashion forward of the back span. Opposite back span 32, leg portions 34, 36 are bent inward to form staple end segments 40, 42. In a loop shape, two lengths of wire may be disposed across one side of the shape to enclose the shape, as demonstrated by the end segments 40, 42. Staple legs portions 34, 36 are bent at end segments 40, 42 to make one of the leg portions at least one wire diameter longer in length than the other leg portion. The longer length of one leg portion (i.e. staple leg 34 in FIG. 2) enables the end segments 40, 42 to lie in a common plane with back span 32. The tips of end segments 40, 42 are angled to form sharp prongs 46 for piercing tissue.

FIG. 3 shows staple 30 in a second, intermediate deploying condition. In this intermediate state, staple legs portions 34, 36 are bent outward to describe a maximum width between the distal tips of the staple legs. In FIG. 3, staple legs 34, 36 are shown expanded open approximately 180° into substantially lateral alignment with the initial back span position, with end segments 40, 42 projecting distally. However, it should be understood that staple legs 34, 36 can be expanded open to an angle less than or greater than 180°. Staple legs 34, 36 are bent outward by applying a deploying force (indicated by arrow 38 in FIG. 2) to a mid section of back span 32 while the staple is held fixed inside at the intersections between the staple legs and back span. The application of force 38 against the opposite, fixed forces at the staple leg intersections pulls the staple legs 34, 36 outward, expanding open the staple, while substantially simultaneously indenting the center of the back span 32. As staple legs 34, 36 are bent outward, back span 32 retains a non-linear characteristic. The outward bending of staple legs 34, 36 creates an enlarged opening into the staple 30 that is preferably in the range of twice the width of the stapler housing. Without a loss in generality, the width may be adjusted for different applications. As an example, the width may be smaller for applications such as mesh fixation.

Staple 30 is transformed to a third, fully deployed form, shown in FIG. 4, by the application of force to laterally spaced points along staple legs 34, 36. This force application is indicated by arrows 44 in FIG. 3. In the final deployment condition, staple leg portions 34, 36 are drawn back towards the center of the staple, with prongs 46 again pointing inward through the intervening tissue to penetrate and hold the tissue. The length of staple 30 decreases between the initial and final deployment conditions, with an ensuing increase in the staple width, so that the final width dimension of the formed staple (described by the distance between staple legs 34, 36) is greater than the initial width dimension. During deployment, staple 30 transitions between the initial, intermediate, and final formed conditions in a series of steps which may be substantially simultaneous, but which are preferably carried out sequentially, so as to first open staple 30 to the intermediate condition of FIG. 3, and then bend each of the staple legs 34, 36 back around into the formed condition shown in FIG. 4. Staples used in this application are preferably biocompatible, implantable, and may optionally be absorbable. A non-limiting list of candidate materials includes: metals such as titanium and its numerous alloys, stainless steel, nitinol, magnesium, and iron; plastics such as PEEK, Prolene™; absorbable materials such as PDS™, Vicryl™, and polylactic acid (PLA); and combinations of these classes of materials. Further, these fasteners may contain therapeutic agents that are selectively or immediately released over time to aid in healing, prevent infection (e.g., triclosan), reduce swelling or edema, etc.

The staple shown in FIGS. 2-4 is intended to be one non-limiting example of a closed-form staple with substantially parallel legs. Additional detail regarding staple designs, as well as staple applicators, procedure applications, and methods of use are disclosed in co-pending U.S. patent application Ser. No. 12/359,351 filed Jan. 26, 2009 entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/359,354 filed Jan. 26, 2009, entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/359,357 filed Jan. 26, 2009 entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/608,860 filed Oct. 29, 2009, entitled "BOX STAPLE METHOD WHILE KEEPING SAID BACK SPAN IN SUBSTANTIALLY ITS ORIGINAL SIZE AND SHAPE", co-pending U.S. patent application Ser. No. 12/609,336 filed Oct. 30, 2009, entitled "A METHOD FOR APPLYING A SURGICAL STAPLE", and co-pending U.S. patent application Ser. No. 12/690,311 filed Jan. 20, 2010 entitled "METHOD FOR FEEDING STAPLES IN A LOW PROFILE SURGICAL STAPLER", which are hereby incorporated herein by reference in their entirety. In applying the staple designs disclosed in the cited US patent applications to the present invention, the staple designs would preferably include a non-linear back span. In addition to the staple designs disclosed herein, it is anticipated that other alternative staple designs may also be conceived and used with the present invention without departing from the scope of the invention.

Figure 5:
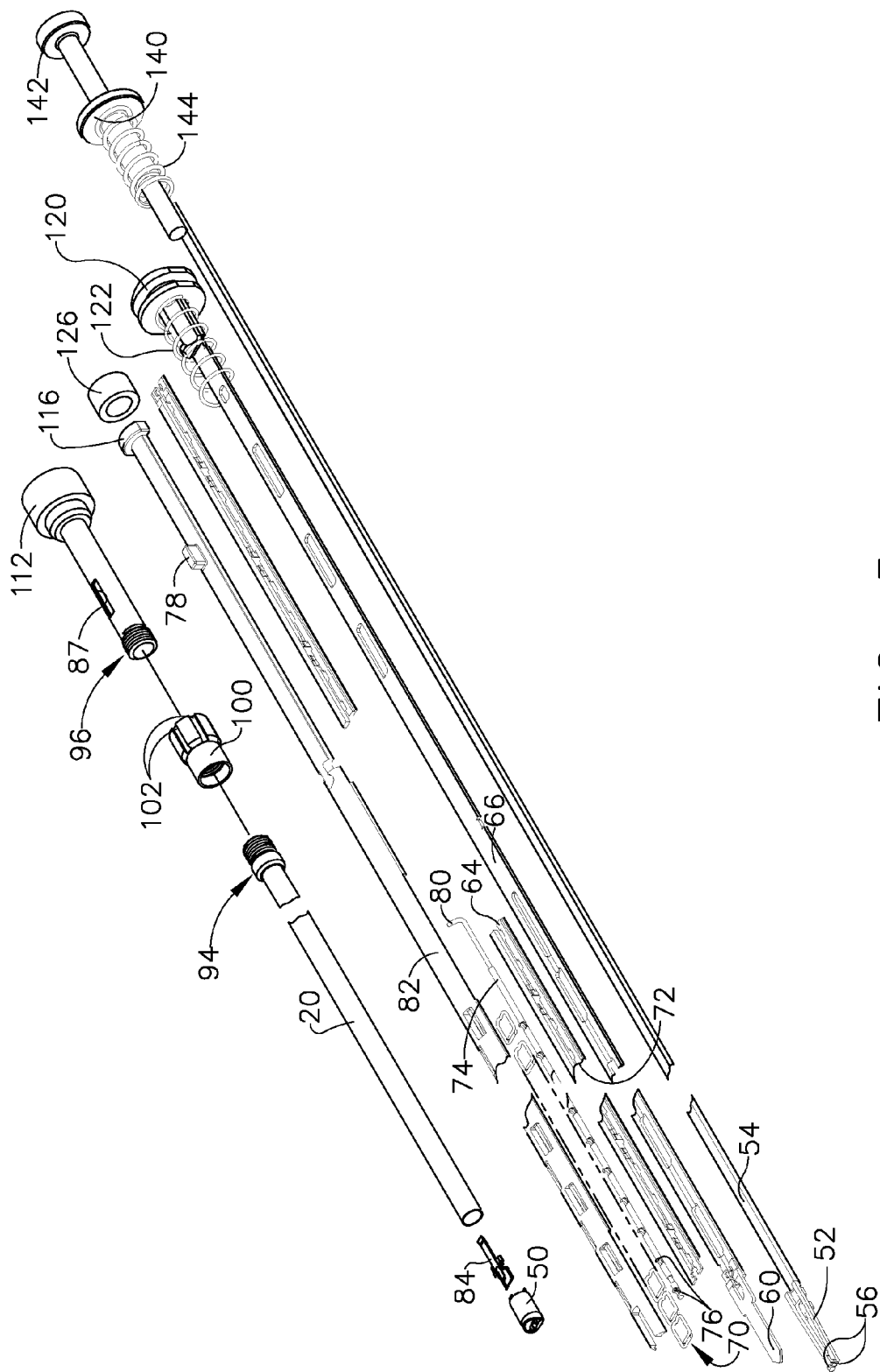
FIG. 5 is an exploded isometric view of the staple housing and deploying assembly for the stapler of FIG. 1.

Turning now to FIG. 5, which shows an exemplary staple deploying assembly for deploying staples 30 in accordance with the invention. As shown in FIG. 5, stapler 10 includes a staple former 50 attached to the distal end of staple housing 20 for forming and closing staples. Staple deployment opening 22 is located at the distal end of former 50. Former 50 includes an inner channel (not shown) for conveying staples through the former and outside the stapler during deployment. Staples 30 are individually conveyed through former 50 and distal opening 22 by an anvil 52. Anvil 52 includes a pair of longitudinally extending, inwardly biased spring arms having upwardly curved, staple holding tines 56 at the distal end. The proximal face of each anvil tine 56 is preferably rounded with an inward radius to aid in positioning and retaining a staple on the tines during deployment. Individual staples are held against the anvil tines during passage through the former 50. The proximal end of anvil 52 is shaped for connecting the anvil to an anvil extension 54. Anvil extension 54 extends proximally from anvil 52, through housing 20, and inside handle 12.

A staple clamp 60 extends substantially along the surface of anvil 52. Clamp 60 comprises an elongated strip having substantially planar upper and lower surfaces and a width slightly narrower than the width of the unformed staples 30. Clamp 60 preferably has as small a length as necessary to cover the anvil 52. The distal end of clamp 60 is shaped for mating engagement with staple back span 32 for engaging and pushing the staple through former 50. The distal end of clamp 60 is angled inwardly to a center tip at approximately a 45° angle relative to the longitudinal stapler axis, although lesser or greater angles may be used to vary the opening size of the staple. The angled clamp tip includes an inward radius for mating against the outer circumference of the staple back span 32. Anvil 52 combines with the distal face of clamp 60 and former 50 to form the discharge channel of the staple deploying assembly. During the deployment sequence, clamp 60 advances distally within the discharge channel to deform the back span of a staged staple and thereby open the staple.

The proximal end of clamp 60 is attached to a driving assembly in handle 12 via a clamp extension. The clamp extension includes an upper section 64 and a lower section 66. Upper clamp extension 64 comprises an elongated, planar strip supporting a staple stack 70. A longitudinally-extending trough 72 is located midway across the width of upper extension 64, beneath staple stack 70, and extends from the distal end beyond the proximal end of the staple stack. Lower clamp extension 66 has an elongated, grooved surface to accommodate trough 72. A staple driving member comprising a substantially rigid, cylindrical rod 74 is retained within trough 72 in a spaced relationship from the plane of staple stack 70. A plurality of outwardly projecting staple advancers 76 are evenly spaced apart substantially along the length of rod 74. Staple advancers 76 extend to at least the proximal end of staple stack 70 to ensure that a staple advancer engages the proximal-most staple in the stack. The proximal end of staple driving rod 74 is curved at approximately a 90° angle relative to the longitudinal rod axis to form a control pin 80.

Rod 74 is retained within trough 72 so as to translate distally and then back proximally with the clamp extension during each staple deployment. Additionally, rod 74 rotates within trough 72 about the longitudinal rod axis. Upper clamp extension 64 includes a plurality of notches spaced apart along a side of trough 72. The notches are aligned with staple advancers 76 to allow the advancers on rod 74 to rotate out of trough 72 and above the surface of the clamp extension. The distal end of rod 74 extends through an open distal end of trough 72 into clamp 60. The staple advancer at the distal end of rod 74 is located in a groove in the proximal end of clamp 60. Rod 74 rotates relative to clamp 60, with the distal-most staple advancer extending up through a notch in the clamp. Rod 74 and the attached staple advancers 76 are advanced and retracted by the clamp extension to index staple stack 70 distally approximately one staple length during each staple deployment.

A staple guide 82 is located proximal of former 50 inside staple housing 20. The outer perimeter of staple guide 82 is shaped to conform to the inner circumference of staple housing 20 to enable the staple guide to extend concentrically within the staple housing. Staple guide 82 is fixed at a proximal end within the stapler handle 12 by a key 78 to prevent translation of the guide along the longitudinal housing axis during staple deployment. Distal housing bushing 106, into which key 78 extends, includes two notches 108 located 180 degrees apart on the circumference of bushing 106 to permit the staple guide 82 to rotate with staple housing 20 about the longitudinal housing axis for positioning the staple prongs 46. A slot 87 is formed in staple housing 20 adjacent guide key 78. Guide key 78 extends up through slot 87 to allow staple housing 20 to translate along the longitudinal housing axis relative to the fixed staple guide 82.

Staple guide 82 includes a plurality of flexible, longitudinally-spaced anti-backup arms 83 (shown in FIG. 13) extending in the direction of staple stack 70. The anti-backup arms flex in and out of contact with the staples in stack 70 to prevent the stack from moving proximally within the staple housing during the staple deployment sequence. Proximal of the anti-backup arms, a closed, contoured guide path (not shown) is formed into the surface of staple guide 82 facing control pin 80. Control pin 80 extends into and rides along the guide path to translate staple driving rod 74 relative to the fixed staple guide 82. While control pin 80 transverses the guide path, the angular direction of the pin changes. The directional changes of control pin 80 rotate rod 74 within trough 72. As rod 74 rotates, staple advancers 76 are rotated from a position inside trough 74 to a position above the surface plane of upper clamp extension 64. Above clamp extension 64, the staple advancers 76 rotate up into the closed loops of the staples in stack 70. The guide path includes a forward track, in which control pin 80 pivots to rotate stapler advancers 76 up inside the loops of staples 30 to advance the staple stack; and a return track, in which control pin 80 pivots to rotate the staple advancers down into trough 72 to allow the staple advancers to retract beneath the advanced staple stack, back to the initial position.

Staple stack 70 extends longitudinally through housing 20, between staple guide 82 and clamp extension 64, in a plane parallel to the longitudinal axis of the housing. Staples 30 are conveyed within stack 70 to the distal end of the stapler prior to deployment. Within stack 70, each staple 30 is oriented such that the abutting end segments 40, 42 of the staple are positioned nearest the open stapler end 22. Within the staple stack, staples may be spaced apart from other staples, in contact with other staples, or alternate between states of contact and spaced. The legs 34, 36 of each staple 30 are aligned substantially parallel to and may be in contact with the walls of staple guide 82 to maintain the forward orientation of the staples. Any number of staples 30 can be included within stack 70, with the preferred stapler embodiment capable of holding 20 or more staples to facilitate procedures, such as GVR, which require a large number of tissue appositions or junctions. The distal end of staple stack 70 is conveyed along the surface of clamp 60 prior to the dropping of the individual staples onto anvil 52 for deployment.

Figure 6:
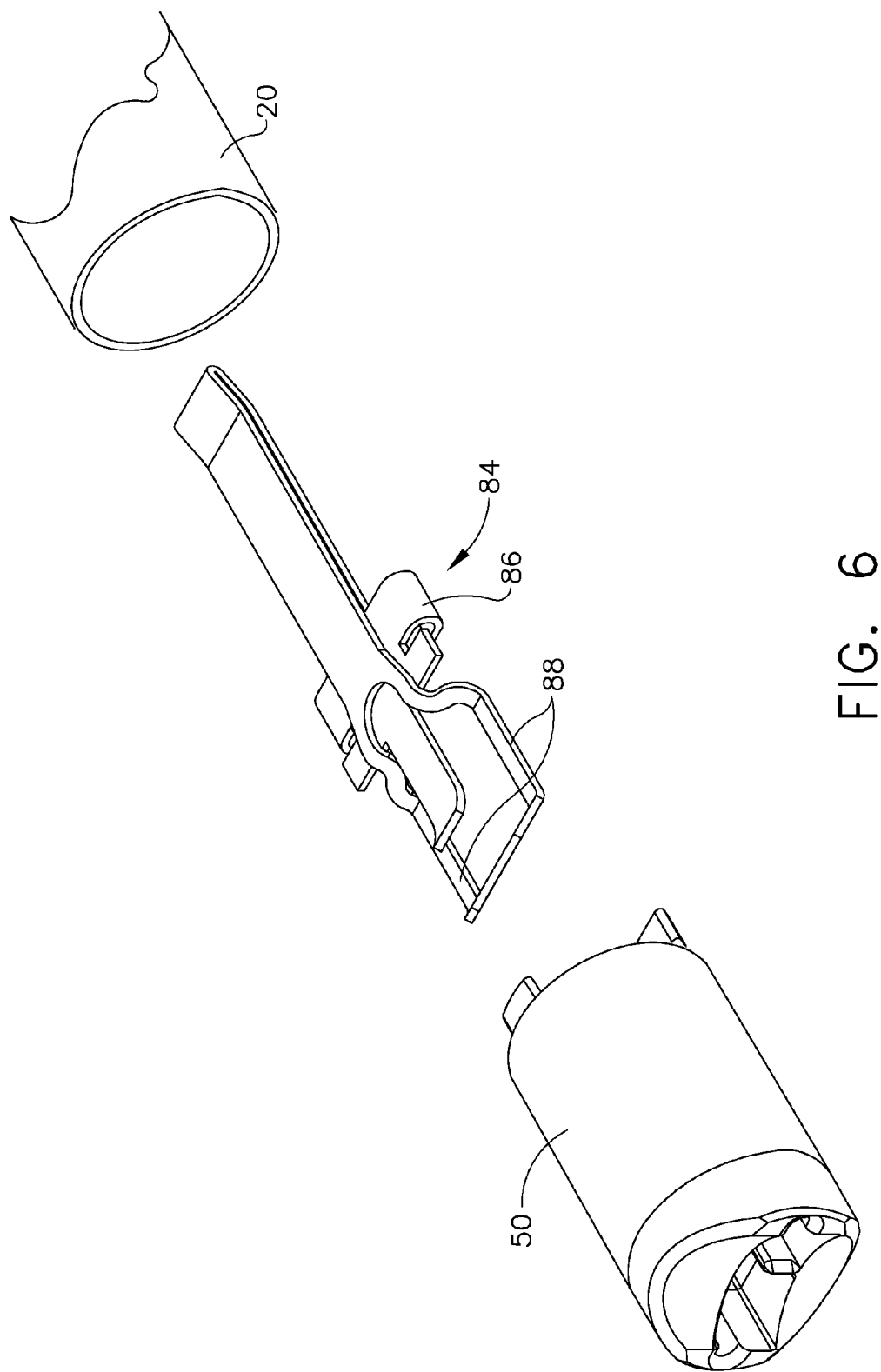
FIG. 6 is an exploded isometric view, partially in section, of the former, shoe and staple housing of FIG. 5.

Staple stack 70 is adjacent to the inner surface of staple guide 82 to enable the anti-backup arms 83 to contact the staples within the stack. As shown in FIGS. 5 and 6, a staple transporter or shoe 84 extends from the distal end of staple guide 82 into former 50 for transferring staples from stack 70 onto anvil 52. Shoe 84 is cantilevered between staple guide 82 and former 50 with the pivot point at the proximal end within the staple guide. The distal end of shoe 84 flexes to index a single, distal-most staple in stack 70 from the surface of clamp 60 into a staging position on anvil 52 during each deployment sequence. The proximal end of shoe 84 is shaped to facilitate movement of staples beneath the shoe as the stack 70 is advanced through housing 20 beneath staple guide 82. The staple advancer 76 at the distal end of staple driving rod 74 pushes the next staple in the stack 70 under shoe 84 during each deployment cycle. Shoe 84 includes a C-channel, indicated at 86, through which the distal end of staple stack 70 passes. The lower sides of C-channel 86 are co-planar with the staple conveying surface of clamp 60 to pass the staple stack 70 through the channel as the stack is advanced along the surface of the clamp. C-channel 86 aids in maintaining staple alignment at the distal end of stack 70, and prevents the distal-most staple in the stack from prematurely tilting into the discharge channel during retraction of clamp 60.

During the staple deployment process, clamp 60 moves distally through the discharge channel, advancing against the back span of a staple 30, and pinning the staple between the distal clamp tip and anvil tines. As clamp 60 advances, the distal end of shoe 84 flexes up against a downward bias by the contact between the advancing clamp and the proximal sloped surfaces of shoe side rails 88. As the distal-most staple moves underneath shoe side rails 88, the side rails push the staple legs 34, 36 down onto clamp 60. The staple remains in this position, between shoe 84 and clamp 60, and against the proximal face of former 50, during the opening and forming of the previous staple. When clamp 60 retracts following staple forming, shoe 84 pushes the staple downward into the discharge channel between the distal clamp face and retracting anvil tines, thereby staging the staple for the next deployment sequence. In the present invention, the staple deploying components within housing 20 are substantially the same size as the pre-deployment staples 30, in order to maximize the staple size and, thus, tissue purchase during deployment, while maintaining a small (3-5 mm) profile for the stapler. The distal deployment opening 22 in former 50 is sized to allow clamp 60, anvil 52, and the deploying staple 30 to pass outside of the former during the deployment process, while the proximal face of the former serves as an end stop for staple stack 70. Additional details regarding the staple deploying assembly can be found in U.S. patent application Ser. No. 12/359,351 entitled "A SURGICAL STAPLER FOR APPLYING A LARGE STAPLE THROUGH A SMALL DELIVERY PORT AND A METHOD OF USING THE STAPLER TO SECURE A TISSUE FOLD" and U.S. patent application Ser. No. 12/690,311 entitled "METHOD AND APPARATUS FOR FEEDING STAPLES IN A LOW PROFILE SURGICAL STAPLER", which have been previously incorporated into this application by reference.

Figure 7:
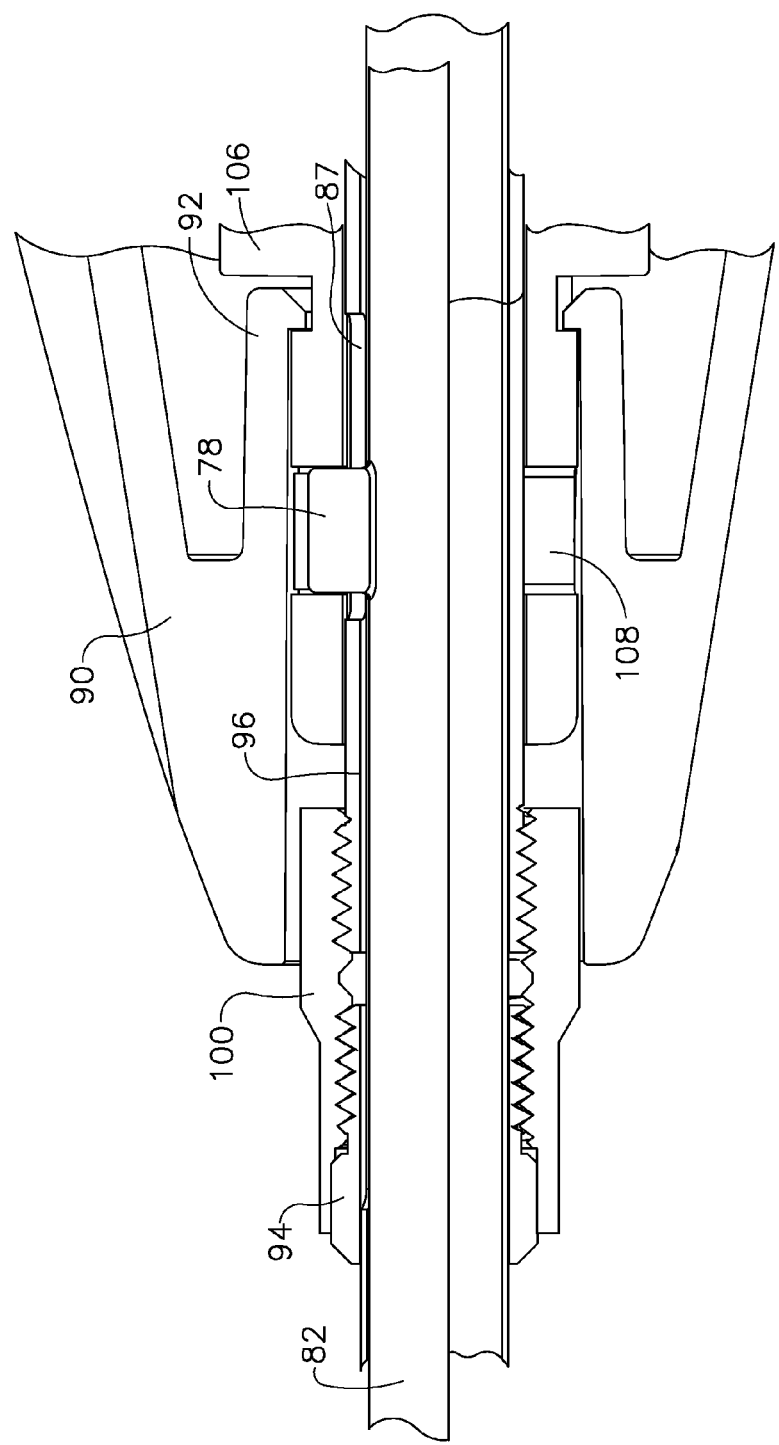
FIG. 7 is a side, partially sectional view of the distal end of the stapler handle.

In a surgical application, stapler 10 is manipulated through a trocar (in a laparoscopic procedure) or flexible endoscopic platform (in natural orifice, endoluminal or transluminal procedures) so that deployment opening 22 is adjacent to the tissue area to be fastened. Staple housing 20 may be rotated relative to handle 12 to change the orientation of deployment opening 22. As shown in FIG. 7, one manner of rotating housing 20 is by way of a knob 90 connected about the circumference of the housing. Knob 90 includes a flange 92 which rotates within a slot at the distal end of handle 12. The location of flange 92 within the handle slot allows rotation of knob 90 about the longitudinal housing axis, while preventing the knob from translating along the axis. As knob 90 is rotated, housing 20 is in turn rotated by a connection between the housing and the knob. A connection also exists between knob 90 and the staple deploying assembly inside of housing 20 to rotate the deploying assembly in conjunction with the housing about the longitudinal housing axis. Accordingly, as housing 20 rotates, the legs of staple 30 rotate relative to the surrounding tissue, thereby altering the position at which the staple prongs will pierce the tissue during deployment.

As shown in further detail in FIGS. 5 and 7, staple housing 20 may be formed of two separate sections, identified as 94, 96, joined by a connecting member, such as a castle nut 100. The distal housing end, identified at 94, has a threaded end which is screwed into the distal end of nut 100. The proximal housing end, identified at 96, also has a threaded end which is screwed into the opposite, proximal end of nut 100. One end of nut 100 has right-handed threads while the opposite end has left-handed threads. The opposite threading allows the two housing sections 94, 96 to be adjustably connected together via the nut 100. Either section 94 or 96 of the staple housing can be rotated relative to nut 100 to increase or decrease the effective longitudinal length of the housing. Adjusting the length of staple housing 20 during assembly of the stapler 10 provides tolerancing for slight manufacturing deviations that might otherwise adversely affect the forming and closing of staples at distal deployment opening 22.

Nut 100 includes a plurality of longitudinally extending grooves 102 evenly spaced apart around the outer circumference of the nut. The inner circumference of rotating knob 90 has at least one longitudinally extending rib (not shown) sized to fit within grooves 102. After staple housing 20 is adjusted via nut 100 to the proper deployment length, the nut is rotated slightly to align the nearest nut groove 102 with a groove 104 on the exterior of distal housing bushing 106 (shown in FIG. 9). Knob 90 is then connected over nut 100 and distal housing bushing 106, with ribs inside the knob aligned with and engaging groove 102 on nut 100 and groove 104 on bushing 106. The interaction of the knob rib with the nut and bushing grooves locks the angular position of nut 100, and thereby fixes the longitudinal length of the staple housing 20. The interconnection between the knob rib and nut groove also enables the knob to rotate the housing about the longitudinal housing axis as described above. Stapler 10 is depicted as having a rigid housing 20 for open surgical applications or laparoscopic applications using trocars. However, in alternative embodiments housing 20 may also include at least one articulation joint allowing the housing to deflect in a controlled manner from the primary axis, or be substantially flexible and of an increased length allowing for less invasive, natural orifice (e.g., transoral, etc.) access to regions of the patient requiring a treatment (e.g., within the peritoneal cavity of the patient). In each of these configurations, it is conceived that the device may also be compatible with a single trocar containing multiple ports.

Figure 8:
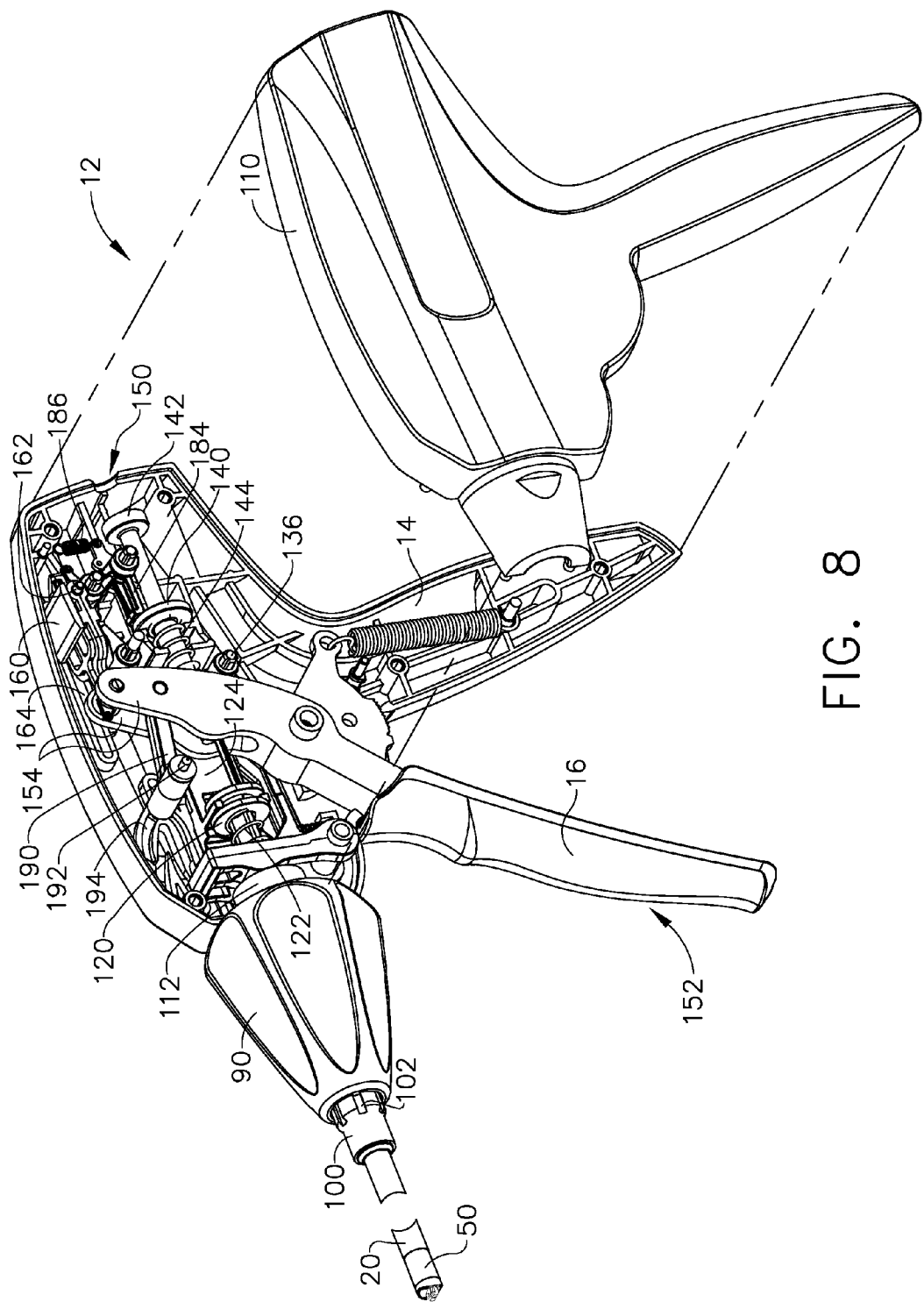
FIG. 8 is an isometric view of the stapler of FIG. 1, shown with a portion of the left side of the handle casing detached.
Figure 9:
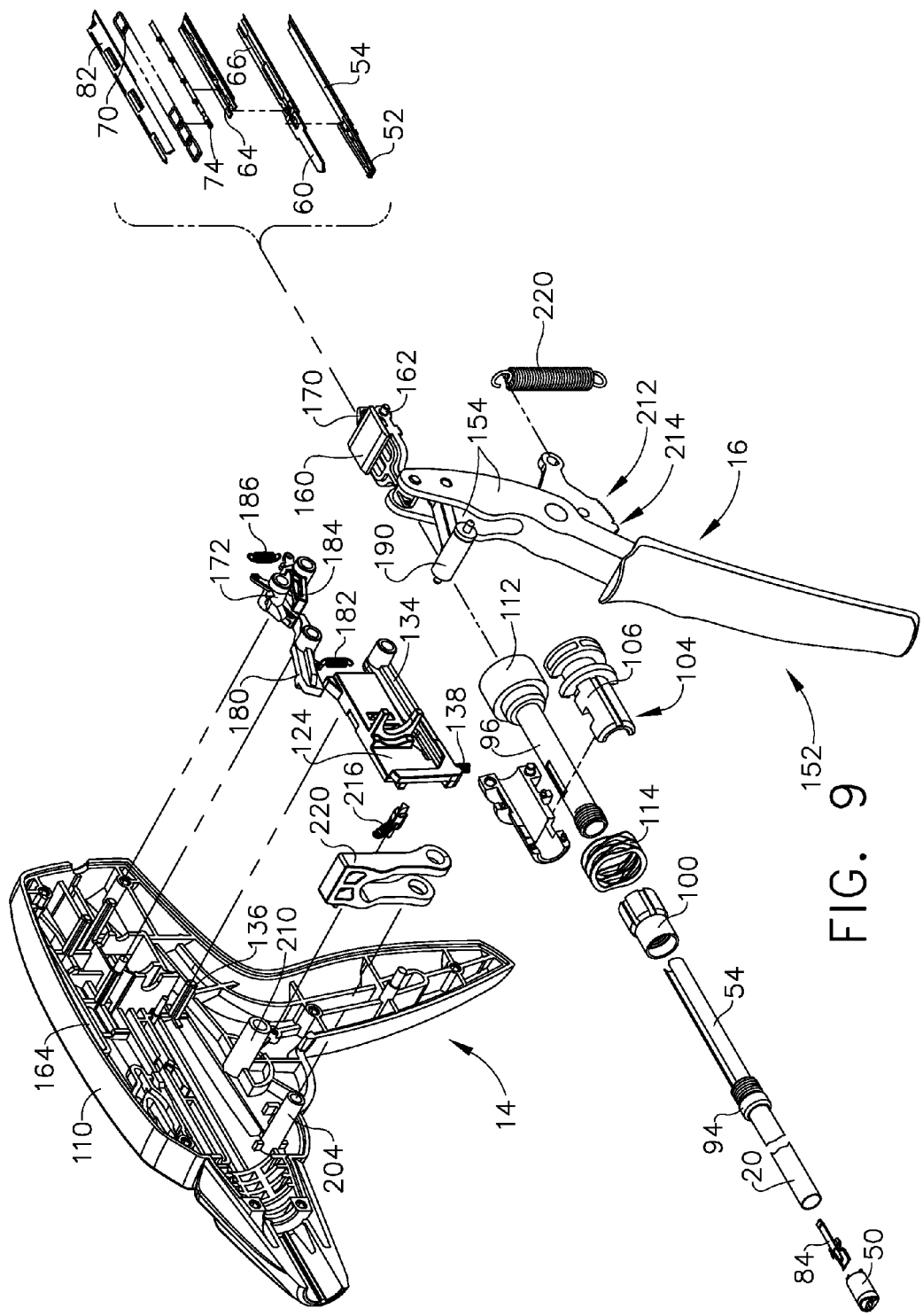
FIG. 9 is an exploded isometric view of the stapler of FIG. 8 shown with the left side of the handle casing removed.
Figure 10:
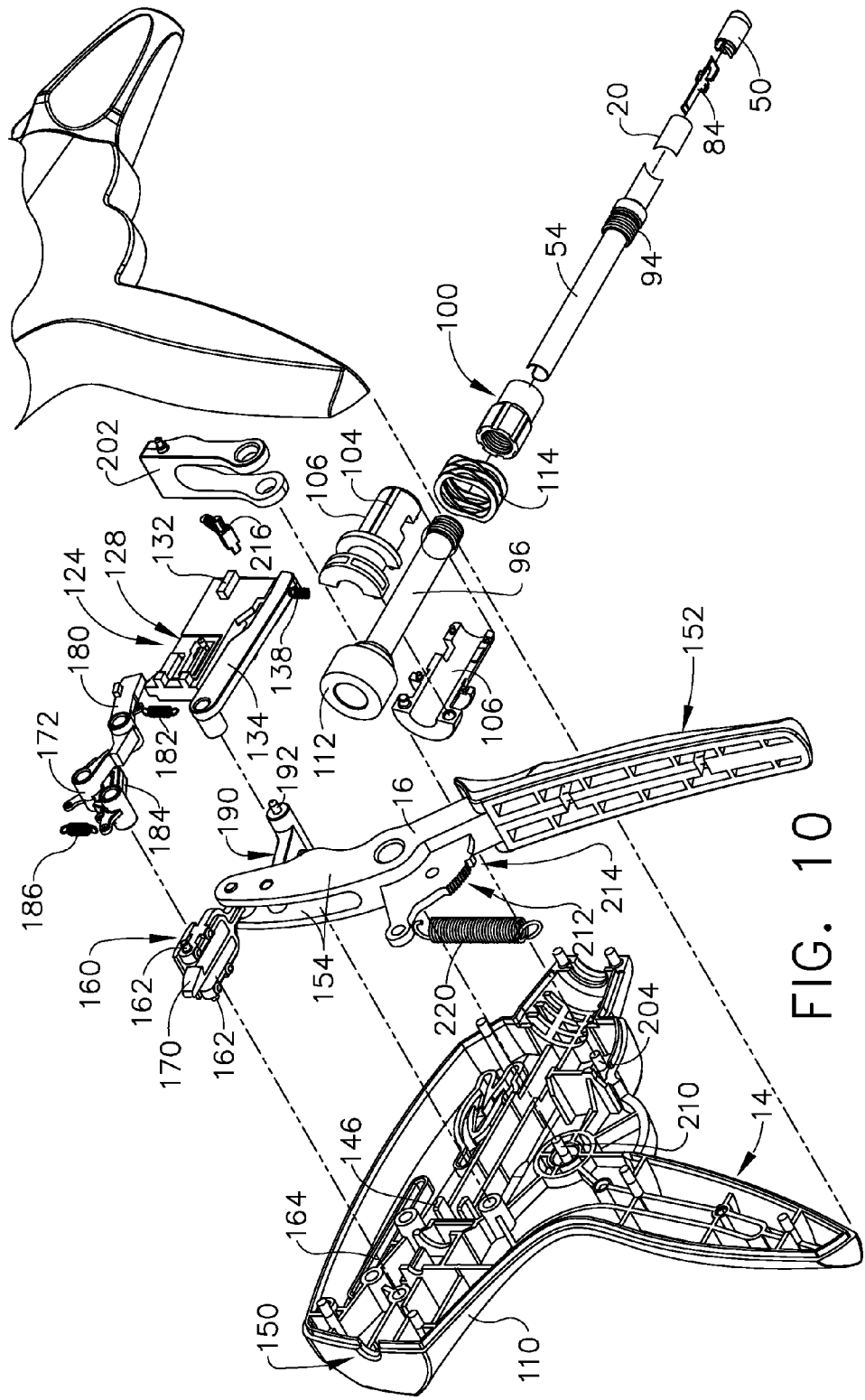
FIG. 10 is an exploded isometric view of the right side of the stapler, showing a number of handle components, viewed from the lower proximal end of the stapler.

Turning now to FIGS. 8-10 which show the proximal, handle end of stapler 10 in an initial deployment position. Handle 12 includes a casing 110 comprising an outer cover with an interior molded frame integrally formed with the cover. Casing 110 may be formed from a plastic or other similar material, in sections which are joined together during the manufacturing process by any of a number of suitable means known in the art. The proximal end 96 of staple housing 20 extends into handle 12, through distal bushing 106, and includes a former bushing 112 at the proximal end. A former return spring 114 encircles housing 20 between the distal face of former bushing 112 and the proximal end of distal bushing 106. Staple guide 82 extends proximally through housing 20 into handle 12. A staple guide stop 116 (shown in FIG. 5) is located at the proximal end of staple guide 82. Staple guide stop 116 holds staple guide 82 stationary with respect to handle 12. Lower clamp extension 66 extends proximally into handle 12 through former bushing 112. The proximal end of lower clamp extension 66 includes a clamp bushing 120. A clamp return spring 122 surrounds clamp extension 66 between clamp bushing 120 and a clamp spring stop 126 (shown in FIG. 12).

Figure 11:
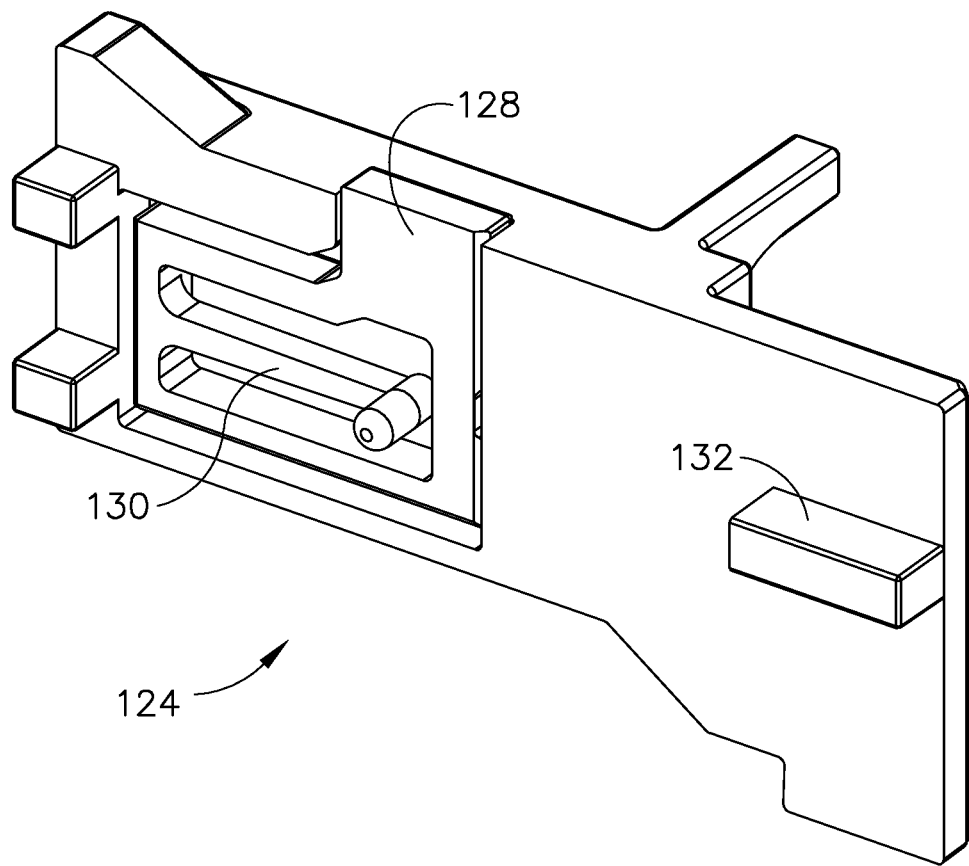
FIG. 11 is a more detailed, isometric view of the right side of the clamp yoke shown in FIG. 10.

Clamp bushing 120 is mounted within the frame of a clamp yoke 124. As shown in greater detail in FIG. 11, clamp yoke 124 includes a clamp lockout member, identified at 128, on a side opposite clamp bushing 120. Clamp lockout member 128 includes a lockout spring 130 which interacts with a lockout tongue 131 on housing casing 110 (shown in FIG. 14) during the staple deployment sequence. The interaction of lockout spring 130 and tongue 131 prevents a stapler jam in the event that actuator 16 is fired too quickly. Clamp yoke 124 also includes a proximal clamp stop 132 which engages a stop in the handle frame to hold clamp 60 in a proximal-most position. As shown in FIGS. 9-10, a clamp L-latch 134 is located beneath yoke 124 and pivots about a pin 136. An L-latch spring 138 biases L-latch 134 in the direction of yoke 124.

Anvil extension 54 extends proximally through the open end of housing 20 and beyond clamp bushing 120. The proximal end of anvil extension 54 includes an anvil stop 140, shown in FIG. 8, with a proximally-extending anvil release member 142. An anvil spring 144 extends between anvil stop 140 and a distal stop, indicated at 146 in FIG. 10, formed into the frame of handle 12. An opening 150 is located in the proximal end of the handle cover for external, operator access to anvil release 142.

Actuator 16 includes a distally facing trigger grip 152 extending outside housing casing 110. Opposite trigger grip 152, actuator 16 is divided into a pair of lobes 154 extending up into the body of handle 12. An anvil latching lever 160 is pivotally connected by a pin between the upper ends of lobes 154 to extend proximally from the actuator. A pair of pins 162 extend laterally from the proximal end of anvil latching lever 160 into a cam path 164 shaped into the interior sides of handle casing 110. Pins 162 are driven along cam path 164 by the motion of actuator 16. Between pins 162, latching lever 160 includes a flexible latching arm 170 having a proximally-extending, tabbed end. A transfer wheel 172 having a plurality of outwardly-extending pawls rotates about a pin adjacent to anvil latching lever 160. In the initial deployment condition shown in FIG. 12, one of the transfer wheel pawls engages the tab at the proximal end of flexible latching arm 170. The contact between the latching arm 170 and transfer wheel 172 rotates the wheel as the latching lever 160 is driven distally along cam path 164. A second pawl on transfer wheel 172 contacts the distal end of a proximal clamp latch 180. In the initial position shown in FIG. 12, proximal clamp latch 180 holds clamp yoke 124 in a forward position. A clamp latch spring 182 biases clamp latch 180 down into the locking position. A third pawl of transfer wheel 172 is positioned adjacent a mating detent on an anvil latch 184. An anvil latch spring 186 is attached to the proximal end of anvil latch 184 to bias the latch into an initial locking position, in which the latch applies a distal force against anvil stop 140 to hold the anvil forward against the force of anvil return spring 144.

A transfer link 190 is also pivotally connected between the actuator lobes 154, below anvil latching lever 160, as shown in FIGS. 8-10. Transfer link 190 extends distal of actuator lobes 154 within the handle 12. The opposite, unattached end of transfer link 190 includes two laterally extending pins 192. Each laterally extending pin 192 engages one of two transfer cam paths 194 formed into opposite sides of the interior of handle casing 110. Each transfer pin 192 rides within cam path 194, completing the full circuitous route as actuator 16 is twice squeezed closed and reopened to deploy a staple. The movement of transfer pin 192 about cam path 194 drives the advancing and retracting of the clamp and former during the staple deployment sequence. Cam path 194 includes a series of four different steps or elevation changes to transition link 190 between the different stages in the deployment sequence, as will be described in more detail below. Actuator 16 includes cam surfaces 200 shaped into the distal faces of lobes 154. Actuator cams 200 are proximally spaced from but aligned to make contact with the proximal face of clamp bushing 120 when the trigger grip 152 is squeezed towards pistol grip 14. A former lever 202 is mounted between former bushing 112 and transfer link 190 to pivot about a pin 204 formed into the handle casing 110. Former lever 202 includes a cam surface that is longitudinally aligned with former bushing 112 to apply a distally directed force to the bushing when the lever is pivoted in the distal direction.

Actuator 16 pivots about a pin 210 that extends through actuator 16 between trigger grip 152 and lobes 154. As shown in FIGS. 10 and 12, actuator 16 includes a handle lockout feature comprising a plurality of ratchet teeth, indicated at 212, ending in a distal release notch 214. A spring-loaded pawl 216 is connected to the frame of pistol grip 14. Teeth 212 are angled to catch pawl 216 as the teeth move proximally over the pawl. Pawl 216 engages successive ratchet teeth 212 as trigger grip 152 is squeezed, to prevent a premature reopening of actuator 16 in the absence of a squeezing force. As actuator 16 pivots to a fully-closed position against pistol grip 14, teeth 212 move proximally beyond pawl 216, pushing the pawl into release notch 214. At release notch 214, the top of pawl 216 rotates clockwise against the angle of teeth 212, allowing the pawl to slide over the teeth back to a proximal-most position. A return spring 220 is connected between actuator 16 and pistol grip 14 for biasing the actuator into an open position. Return spring 220 is connected so that the spring expands as actuator 16 is squeezed closed. Spring 220 returns actuator 16 to an open condition as pawl 216 reaches release notch 216, and the squeezing force on the trigger grip 152 is released.

Figure 14:
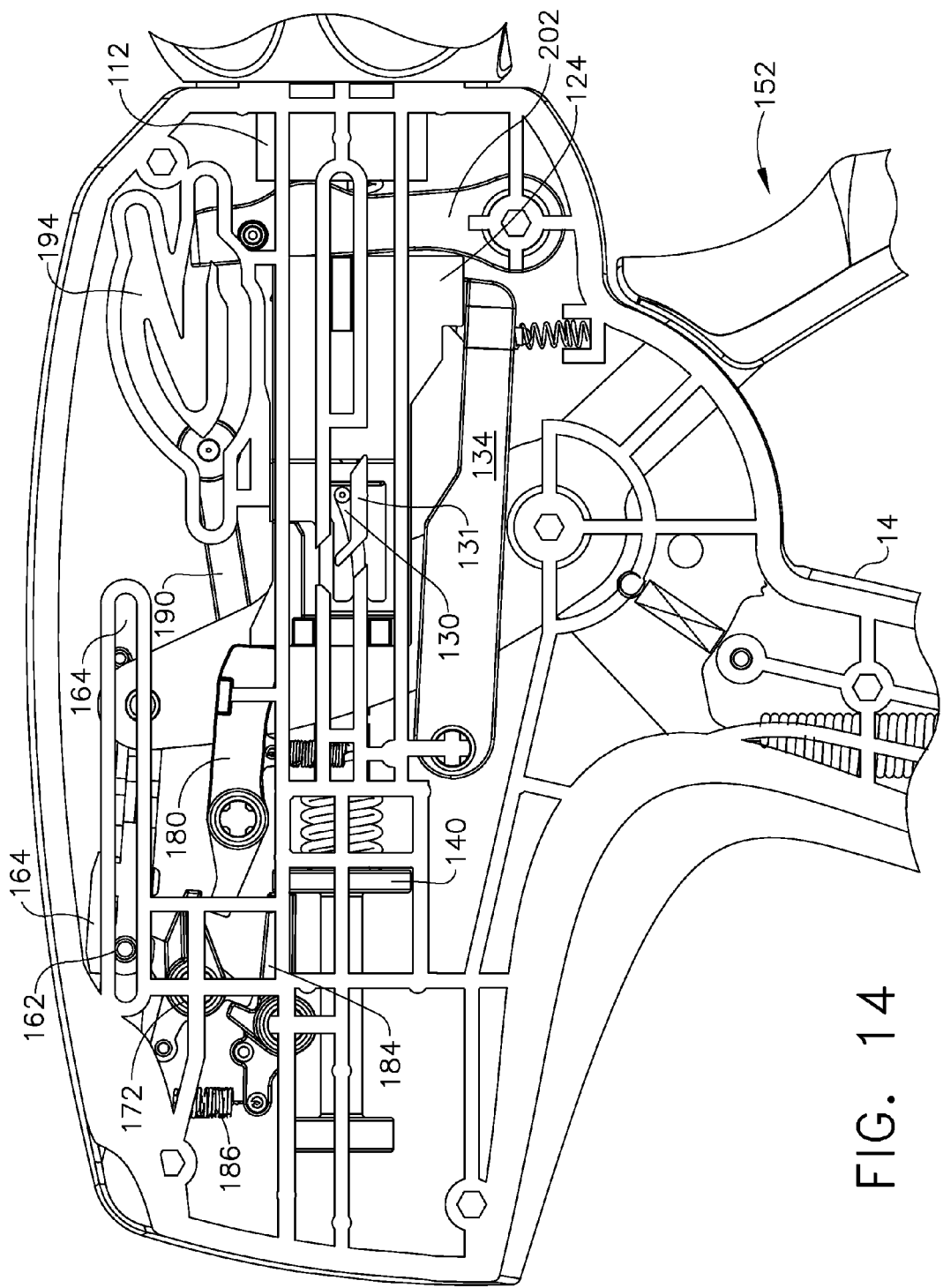
FIG. 14 is a right side view of the proximal end of the stapler in an initial deployment condition, shown with the outer cover removed.

In the initial deployment position shown in FIGS. 12-14, the upper lobes 154 of actuator 16 are in a proximal-most position, with anvil latching lever 160 in a proximal-most position engaging transfer wheel 172. Anvil latch 184 is in a down position with the latch arm pushing against anvil stop 140 to hold the anvil in a distal-most position, as shown in FIG. 13, in which anvil tines 56 extend outside distal deployment opening 22. Proximal clamp latch 180 is also in a downward position in contact with the proximal end of clamp yoke 124 to hold clamp 60 in a forward position, inside deployment opening 22, and beneath the distal-most staple in stack 70. Shoe side rails 88 push the distal-most staple down against the upper surface of clamp 60, while the next staple in stack 70 is held within C-channel 86 on the upper surface of the clamp. Clamp lockout spring 130 is positioned on the upper surface of lockout tongue 131, as shown in FIG. 14, and L-Latch 134 is pushed down by the distal end of clamp yoke 124. In this initial position, transfer link 190 is also at a proximal-most position within transfer cam path 194. Former lever 202 is pivoted away from former bushing 112, allowing former return spring 114 to fully expand, and former 50 to be retracted back proximally from anvil tines 56.

Figure 17:
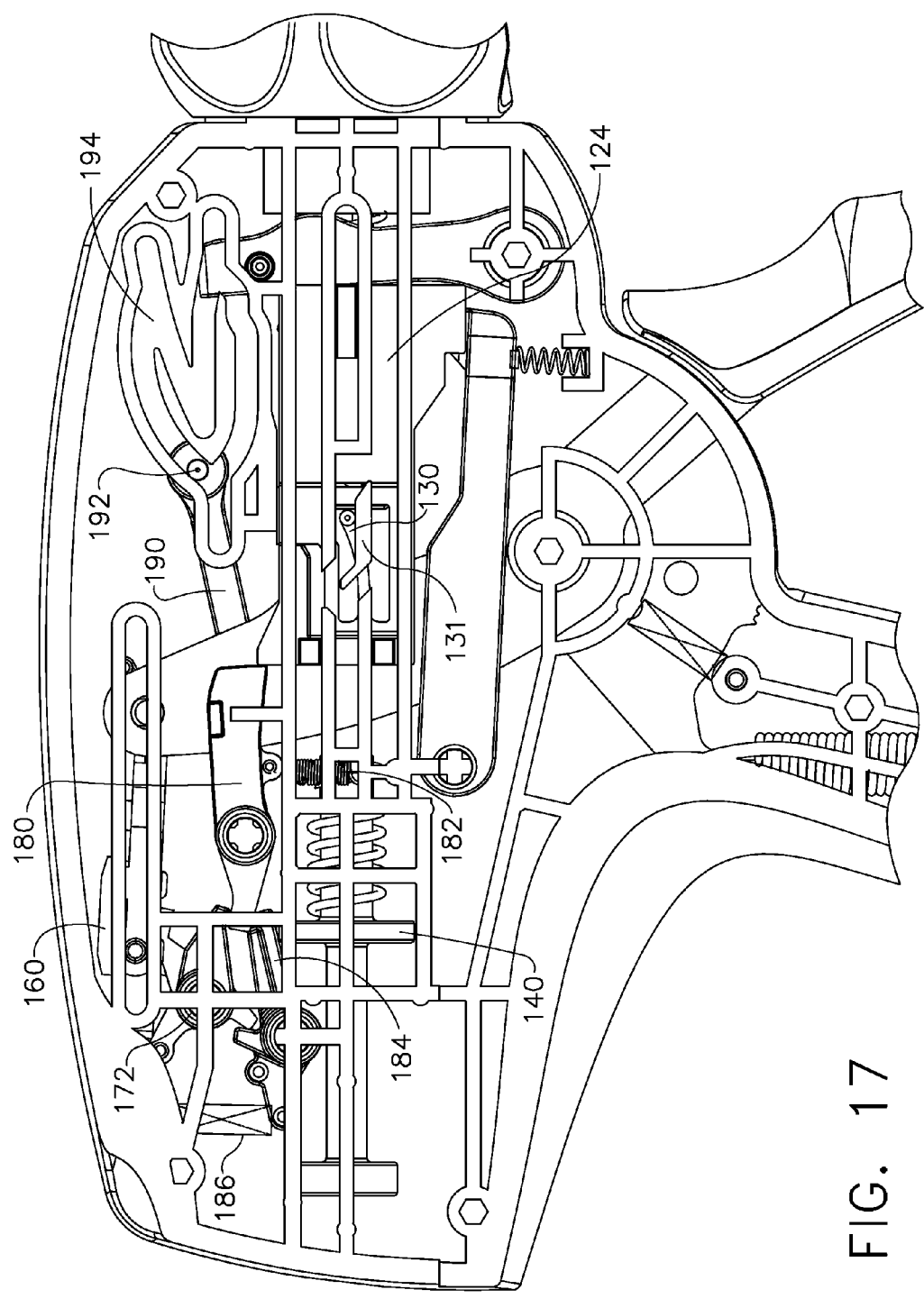
FIG. 17 is a right side view of the proximal end of the stapler with the outer cover removed, showing the same deployment condition as FIG. 15.

To deploy a staple 30, stapler 10 is inserted through a small diameter port or flexible endoscopic platform to reach the desired tissue area inside a body cavity. At the appropriate tissue location, stapler end 22 is placed adjacent the tissue or tissue fold to be stapled, with rotating knob 90 being turned as necessary to position the staple prongs 46. With stapler 30 appropriately positioned against the targeted tissue area, trigger grip 152 is manually squeezed in the direction of pistol grip 14 to begin the staple deployment sequence. As trigger grip 152 is squeezed actuator 16 pivots about pin 210, causing the upper lobes 154 to pivot distally within the handle. The distally moving lobes 154 pull anvil latching lever 160 distally within anvil cam path 164. As latching lever 160 moves distally, latching arm 170 pulls on the first transfer wheel pawl, causing the wheel to rotate. As transfer wheel 172 rotates, the second pawl on the wheel begins to apply a downward force to proximal clamp latch 180. The downward force is initially insufficient to overcome clamp latch spring 182 and release clamp 60 back proximally. Simultaneously, the third transfer wheel pawl applies a proximal force to the detent on anvil latch 184. The force on the anvil latch detent overcomes the force of anvil latch spring 186, pivoting the latch up and out of contact with anvil stop 140, as shown in FIG. 15. As anvil latch 184 pivots away from anvil stop 140, the anvil stop is released to move proximally under the force of anvil spring 144, drawing anvil tines 56 back inside of distal deployment opening 22 and against the distal clamp face, as shown in FIG. 16. Clamp 60 remains locked in position by proximal clamp latch 180, thereby preventing additional proximal movement by anvil 52. As actuator lobes 154 pivot distally, transfer link 190 also begins to drive pin 192 distally up the first leg of cam path 194, as shown in FIG. 17.

Figure 18:
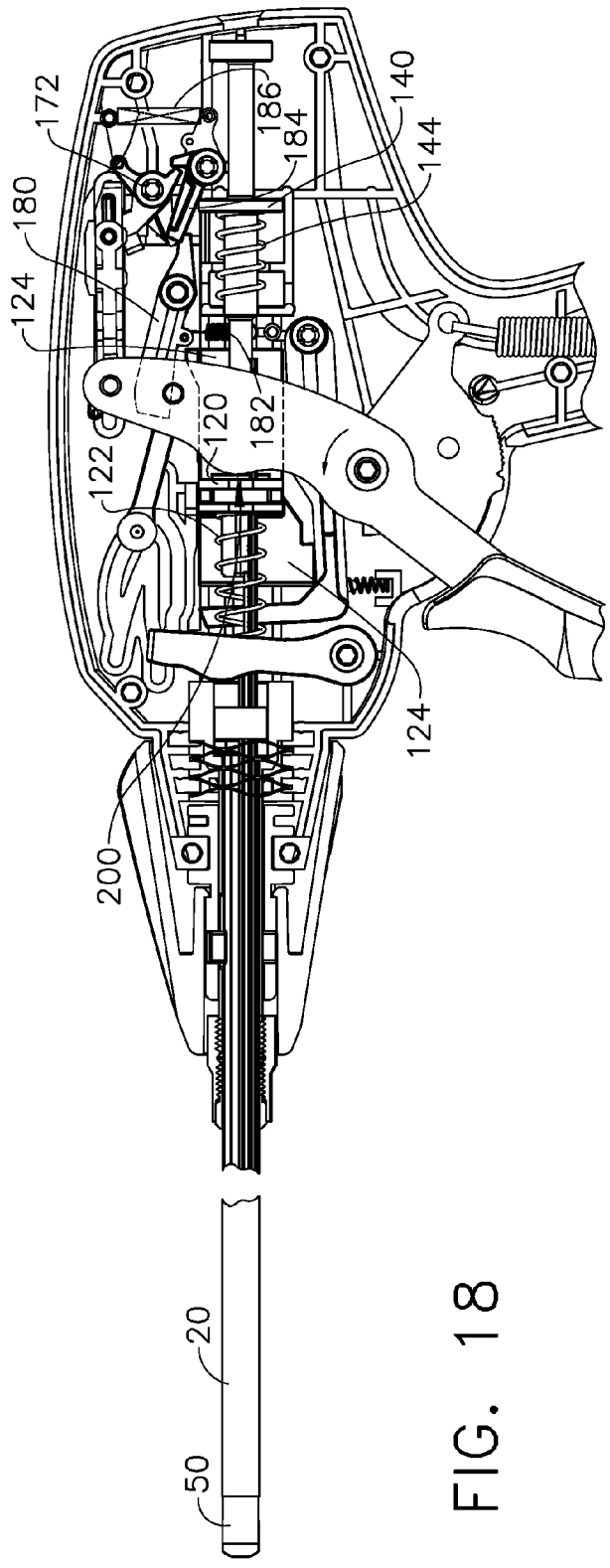
FIG. 18 is a side, partially sectional view of the distal end and handle of the stapler showing the former, anvil and clamp in a proximal-most position.
Figure 19:
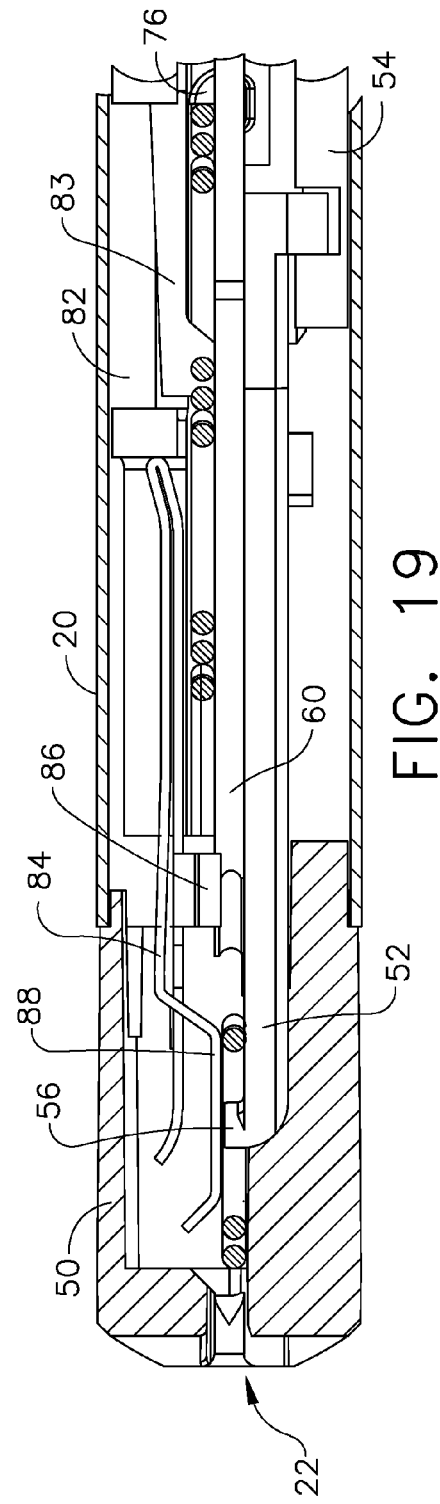
FIG. 19 is a side, partially sectional view showing the distal end of the stapler in the same deployment condition as FIG. 18, with a staged staple being deposited into the discharge channel.
Figure 20:
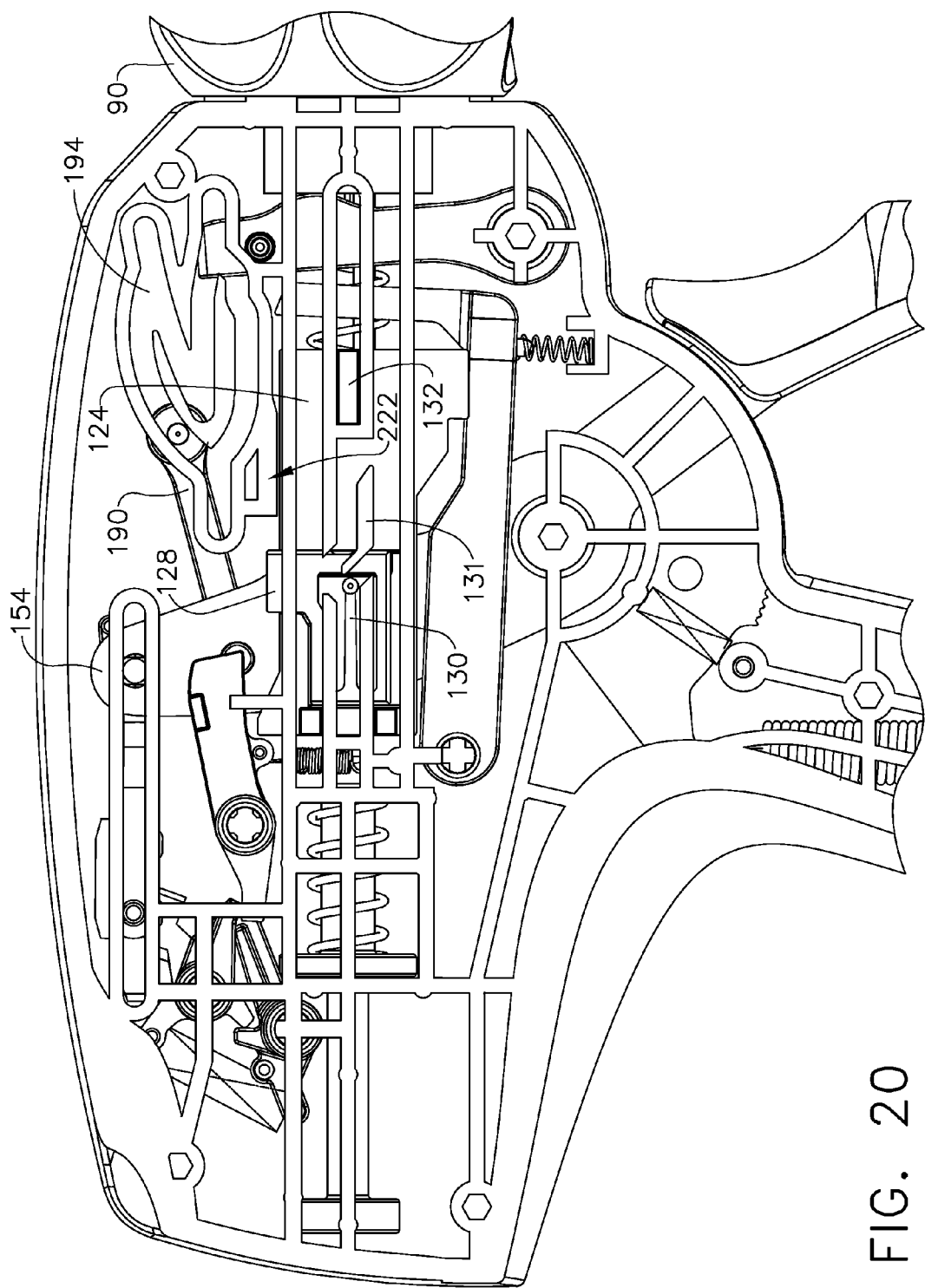
FIG. 20 is a right side view of the proximal end of the stapler with the outer cover removed, showing the same deployment condition as FIG. 18.

As actuator lobes 154 continues pivoting distally, anvil lever 160 moves further distally within anvil cam path 164, rotating transfer wheel 172. The rotating wheel 172 applies increased force to the proximal end of clamp latch 180, overcoming the force of clamp latch spring 182, and releasing clamp yoke 124 to retract proximally under the force of clamp return spring 122, as shown in FIG. 18. Clamp yoke 124 draws clamp 60 proximally until proximal clamp stop 132 bottoms out against the handle frame, as shown in FIG. 20. Anvil 52 retracts proximally with the clamp 60 until anvil stop 140 reaches the proximal end stop in the housing frame, as shown in FIGS. 18 and 20. In this fully retracted position, the tip of clamp 60 is proximal of the distal-most staple in stack 70 and anvil tines 56 are spaced distally forward of the clamp tip. The retracted position of clamp 60 allows shoe 84 to push the distal-most staple down into the discharge channel and over anvil tines 56, as shown in FIG. 19. The proximal stop of clamp yoke 124 positions clamp bushing 120 at the distal face of actuator cams 200.

The proximal movement of clamp yoke 124 also drives lockout spring 130 up and over the proximal tip of lockout tongue 131, as shown in FIG. 20. As the lockout spring 130 drops below lockout tongue 131, the clamp lockout member 128 resets inside clamp yoke 124, allowing the clamp yoke to advance beneath the adjoining frame of the housing casing during subsequent steps in the deployment sequence. In the event that actuator 16 is moved very rapidly, the actuator cams 200 can, in some cases, prevent the clamp yoke 124 (and thus clamp 60) from fully retracting to the proximal end stop. In this event, clamp 60 will remain forward within the discharge channel and prevent the staged staple from dropping properly into the channel. If the staged staple does not drop properly into the discharge channel, a staple jam can occur when the clamp 60 advances distally. To prevent this possibility, lockout spring 130 will get held and fail to drop below lockout tongue 131 on the housing casing if the actuator 16 is moved too quickly. In this event, the lockout spring 130 will keep the lockout member 128 lifted above the surface of the clamp yoke 124, thereby preventing the clamp yoke from advancing distally beneath the adjoining section of the casing frame indicated at 222. To reset the device for normal function, the user fully releases trigger grip 152 to cause lockout spring 130 to drop below lockout tongue 131.

Figure 23:
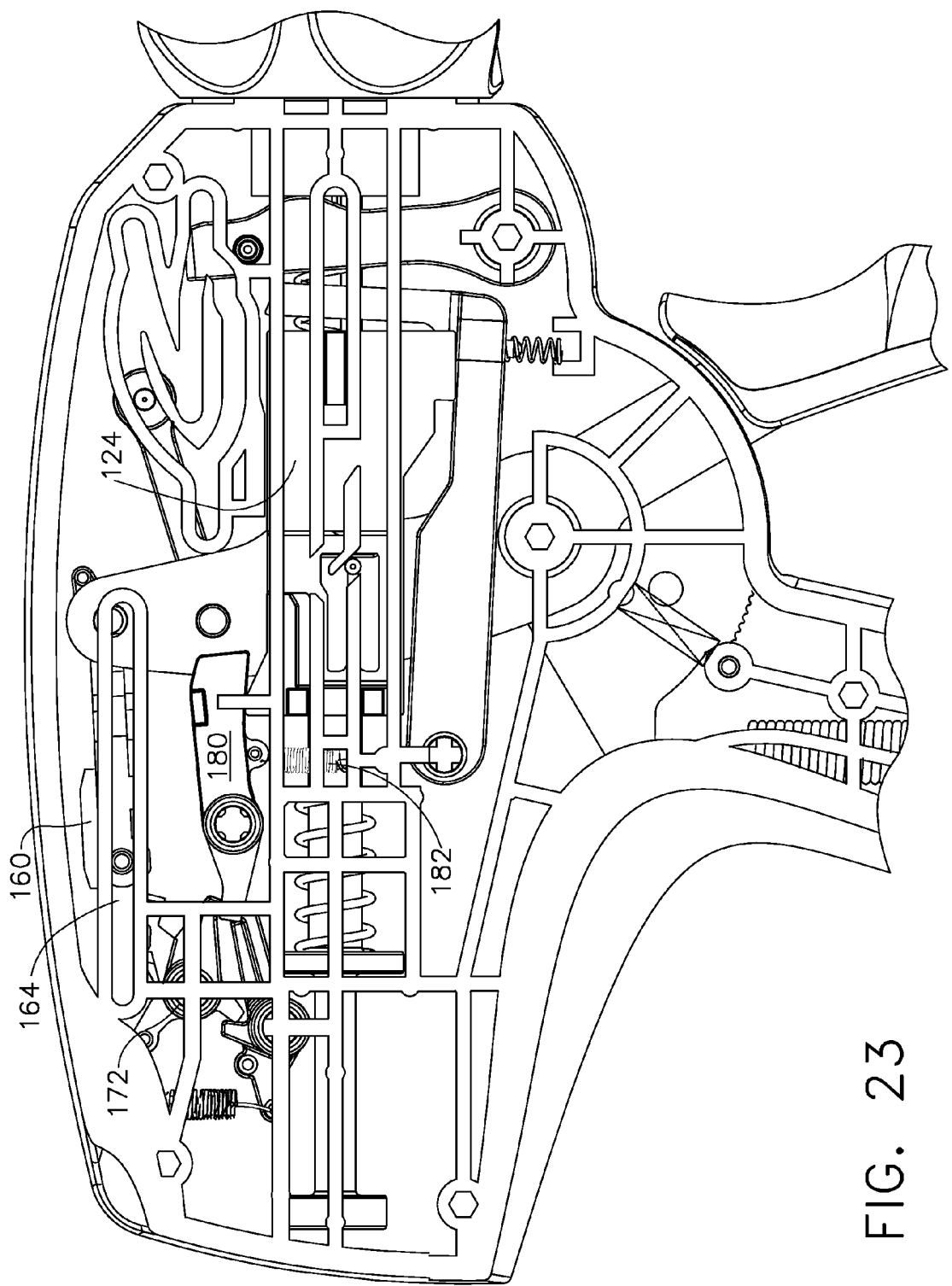
FIG. 23 is a right side view of the proximal end of the stapler with the outer cover removed, showing the same deployment condition as FIG. 21.

As actuator lobes 154 continue pivoting distally from the squeezing force on trigger 152, cam surfaces 200 apply a distal driving force against clamp bushing 120, as shown in FIG. 21. The distal force advances clamp 60 through the discharge channel and into contact with staple back span 32, as shown in FIG. 22. As clamp 60 begins advancing, staple driving rod 74 rotates staple advancers 76 above the surface of clamp extension 64. Staple advancers 76 push staple stack 70 distally as the clamp advances. In addition, the movement of lobes 154 drives transfer link 190 forward up the first leg of transfer cam path 194. At the proximal handle end, anvil latching lever 160 continues moving distally along anvil cam path 164. Anvil latching arm 170 advances distally beyond the first pawl of transfer wheel 172, as shown in FIG. 23, disconnecting the lever 160 from the transfer wheel, and preventing further rotation of the wheel. The release of transfer wheel 172 allows the proximal end of clamp latch 180 to pivot downward under the force of clamp latch spring 182.

This positions the clamp latch 180 to engage the proximal face of clamp yoke 124 as the yoke advances distally beyond the latch.

Figure 24:
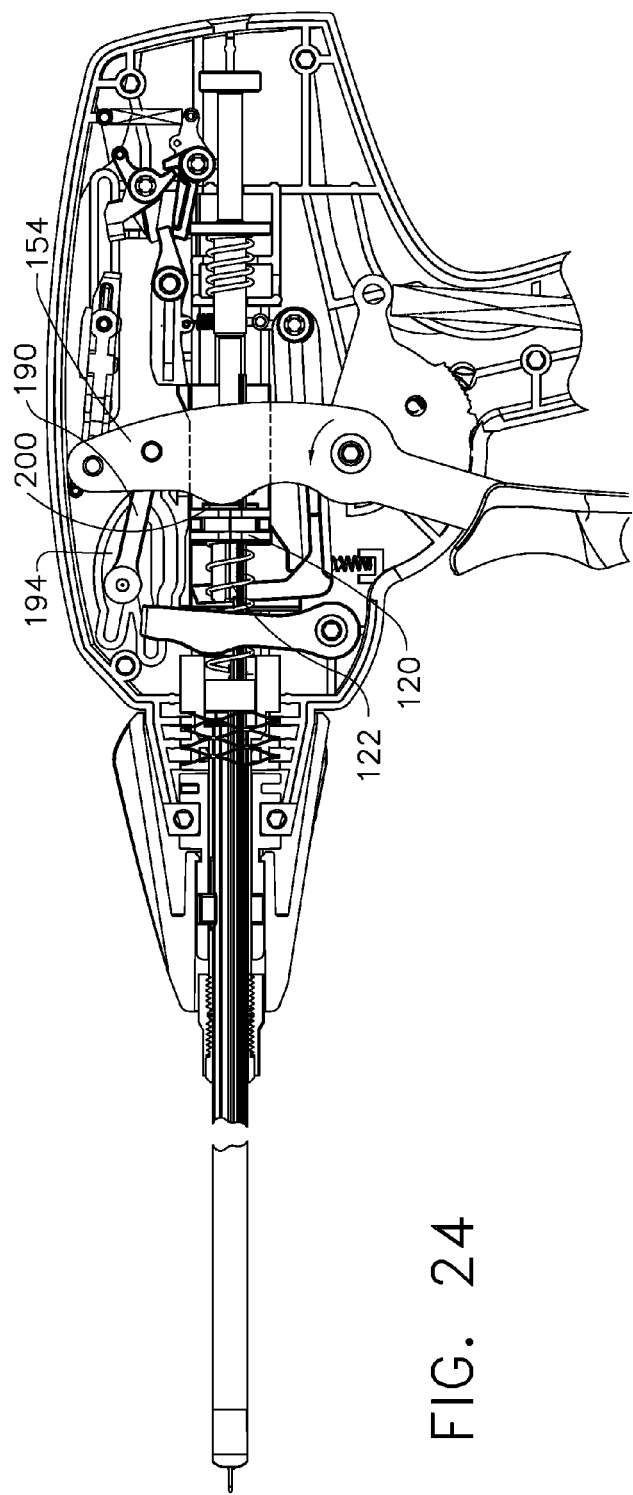
FIG. 24 is a side, partially sectional view of the distal end and handle of the stapler showing a deployment condition in which the actuator advances the clamp and anvil distally.
Figure 25:
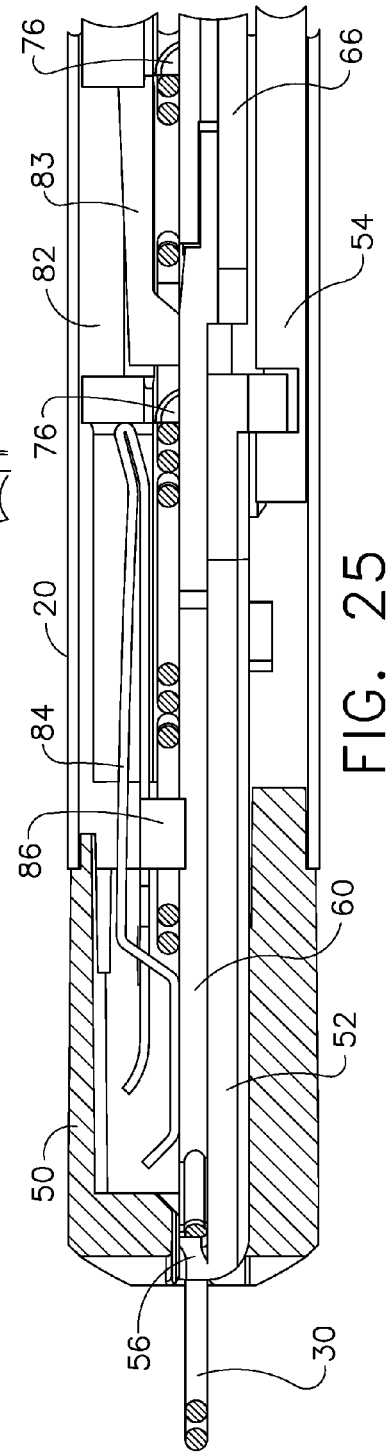
FIG. 25 is a side, partially sectional view showing the distal end of the stapler in the same deployment condition as FIG. 24, with the clamp pushing the staged staple and anvil distally through the deployment opening.
Figure 26:
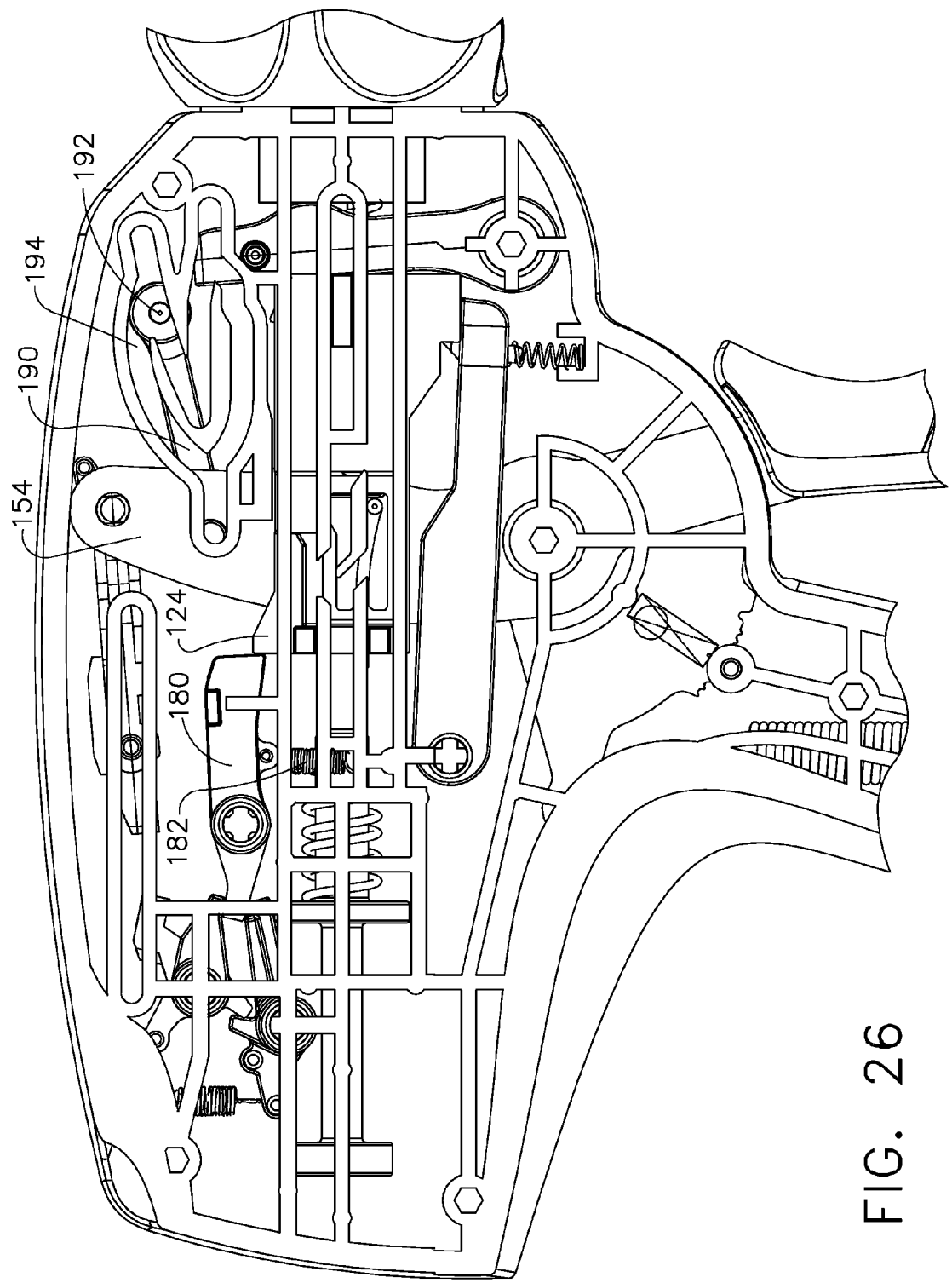
FIG. 26 is a right side view of the proximal end of the stapler with the outer cover removed, showing the same deployment condition as FIG. 24.

Actuator cams 200 continue pushing clamp bushing 120 distally against the force of clamp return spring 122, advancing clamp yoke 124, and allowing clamp latch 180 to pivot down behind the proximal end of the clamp yoke. The distal movement of lobes 154 drives transfer link 190 within cam path 194, dropping the link pin 192 from the first to the second path leg as shown in FIGS. 24 and 26. As clamp 60 advances distally within the discharge channel, the inward radius at the distal clamp tip engages the back span 32 of the staged staple and pushes the staple against the proximal face of the anvil tines 56, holding the staple back span fixed between the clamp and anvil tines. As actuator 16 continues applying force to clamp bushing 120, clamp 60 drives the staple 30 and anvil 52 forward through the open stapler end 22, as shown in FIG. 25. As anvil tines 56 and the staged staple 30 progress through the distal stapler opening, the anvil tines remain inwardly biased, adjacent the intersection between the staple legs 34, 36 and back span 32. With staple 30 held outside the open stapler end by clamp 60 and anvil tines 56, anvil stop 140 bottoms out against the handle casing, as shown in FIG. 27, stopping further distal movement of anvil 52. Anvil latch 184 pivots down into contact with the proximal face of anvil stop 140 to hold the anvil 52 forward outside the open stapler end.

When anvil 52 reaches its fully distal position, as shown in FIG. 28, the back span of staple 30 is firmly held between the tip of clamp 60 and the proximal face of anvil tines 56. After anvil 52 reaches its distal stop, actuator 16 continues advancing clamp bushing 120 and, thus, clamp 60 relative to the fixed anvil tines. As clamp 60 advances, the clamp tip moves between anvil tines 56, pushing the tines outward against the inside surfaces of staple 30 at the intersections between staple legs 34, 36 and back span 32. The advancing clamp tip applies a distally directed force against staple back span 32 between anvil tines 56. The distally directed force of clamp 60 drives the anvil arms out laterally and deforms back span 32 between the anvil tines. The deforming force of clamp 60 against the fixed back span 32 drives the anvil tines 56 laterally into staple legs 34, 36, expanding open the staple 30. As staple 30 is expanding open, staple legs 34, 36 are bent back against the distal angled face of clamp 60. The angle at which staple legs 34, 36 bend open can vary, depending in part upon the angle of the clamp distal tip. As staple 30 expands open from its initial, closed-form shape, prong tips 46 move from an inward, overlapping position to the open, spread position described above, producing an increased width dimension in the staple. The substantial increase in width between the closed, folded staple condition and the open, expanded staple condition enables the staple to obtain a substantial tissue purchase while utilizing a small diameter delivery shaft.

Figure 29:
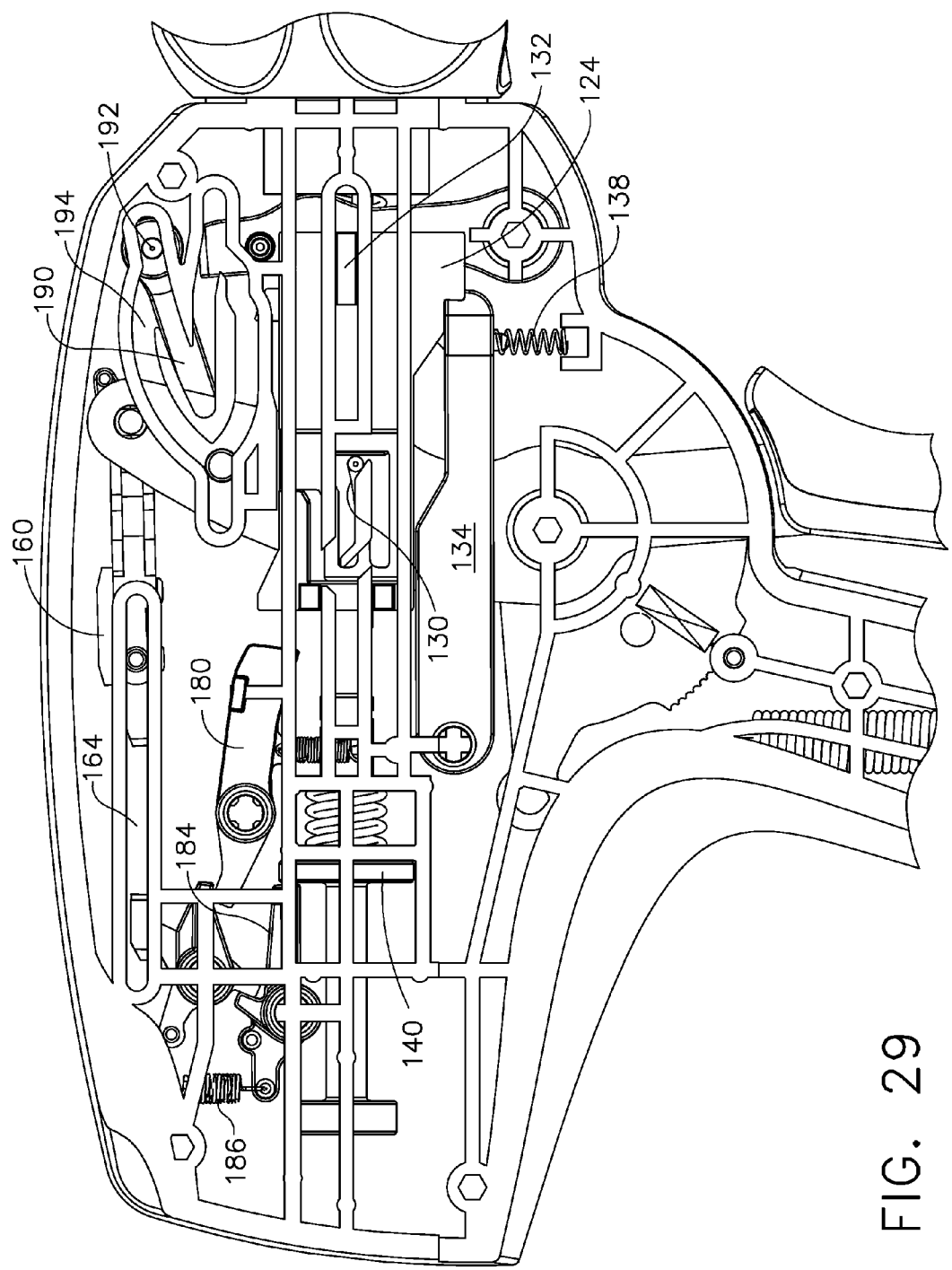
FIG. 29 is a right side view of the proximal end of the stapler with the outer cover removed, showing the same deployment condition as FIG. 27.
Figure 30:
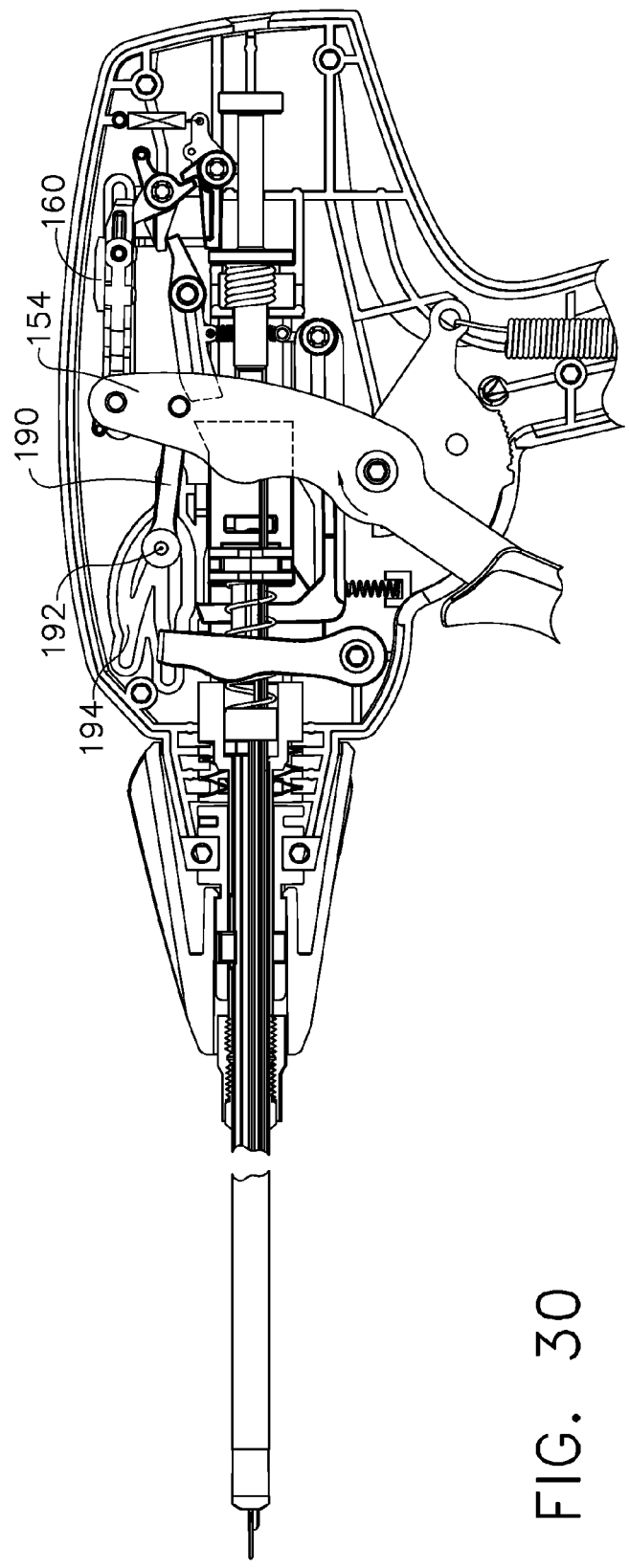
FIG. 30 is a side, partially sectional view of the distal end and handle of the stapler showing a deployment condition in which the actuator is released open during a pause in the deployment sequence.
Figure 31:
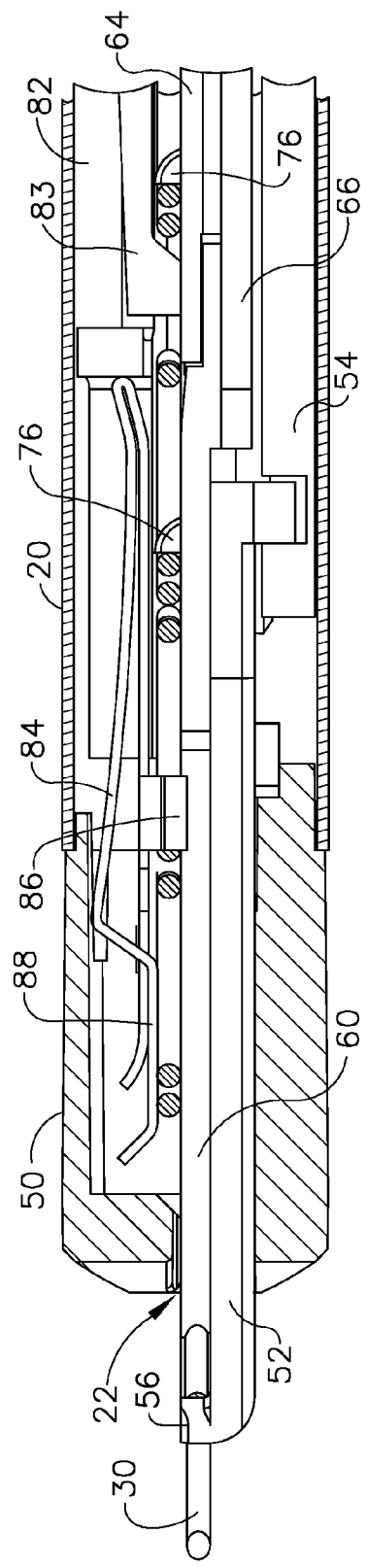
FIG. 31 is a side, partially sectional view showing the distal end of the stapler in the same deployment condition as FIG. 30, with the fully distal clamp and anvil holding the open staple outside the distal deployment opening.
Figure 32:
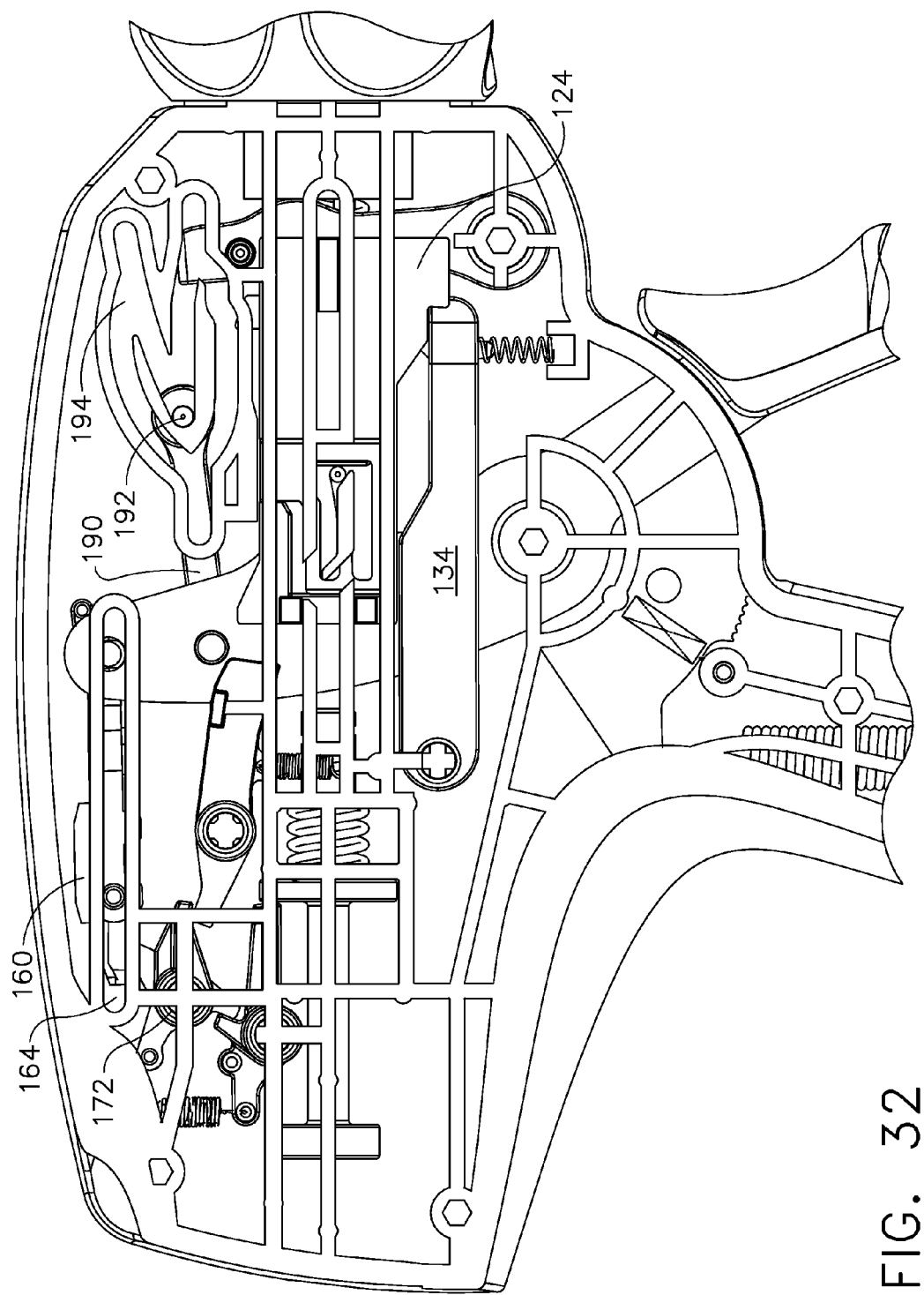
FIG. 32 is a right side view of the proximal end of the stapler with the outer cover removed, showing the same deployment condition as FIG. 30.

Clamp 60 opens staple 30 at the distal end of the clamp advancement. At this point, L-latch 134 springs up into engagement with clamp yoke 124 to lock the clamp forward, with the staple pinned between the clamp and anvil tines. The transfer link 190 has advanced to the distal end of the second leg of the cam path 194, as shown in FIGS. 27 and 29. The distal advance of clamp yoke 124 has also pulled clamp lockout spring 130 back around the distal end of the lockout tongue 131. As staple 30 expands open, actuator 16 pivots to a fully closed position, with lockout pawl 216 advancing to release notch 214. At release notch 214, lockout pawl 216 pivots free of the ratchet teeth 212, allowing actuator 16 to pivot open under the force of actuator return spring 220. As actuator 16 reopens, transfer link 190 is drawn back down the second leg of cam path 194. A step between the first and second cam path legs prevents link pin 192 from reversing back into the first leg of the path. At the proximal end of the second cam path leg, the transfer link pin 192 drops over another step into the proximal end of the third path leg, as shown in FIGS. 30 and 32. At this point in the deployment sequence, actuator 16 does not return to the fully open, initial position due to the more proximal location of the transfer link pin 192 in the cam path 194. Anvil link pin 162 retracts within anvil cam path 164 as actuator 16 pivots open. However, because the actuator 16 does not return to the fully open, initial position, latching arm 170 and transfer wheel 172 remain disconnected. With staple 30 fully expanded and stabilized between clamp 60 and anvil tines 56, as shown in FIG. 31, the release of actuator 16 provides a pause in the deployment process to allow the surgeon to manipulate the open, exposed staple 30 to pierce or otherwise engage the intended tissue.

Figure 35:
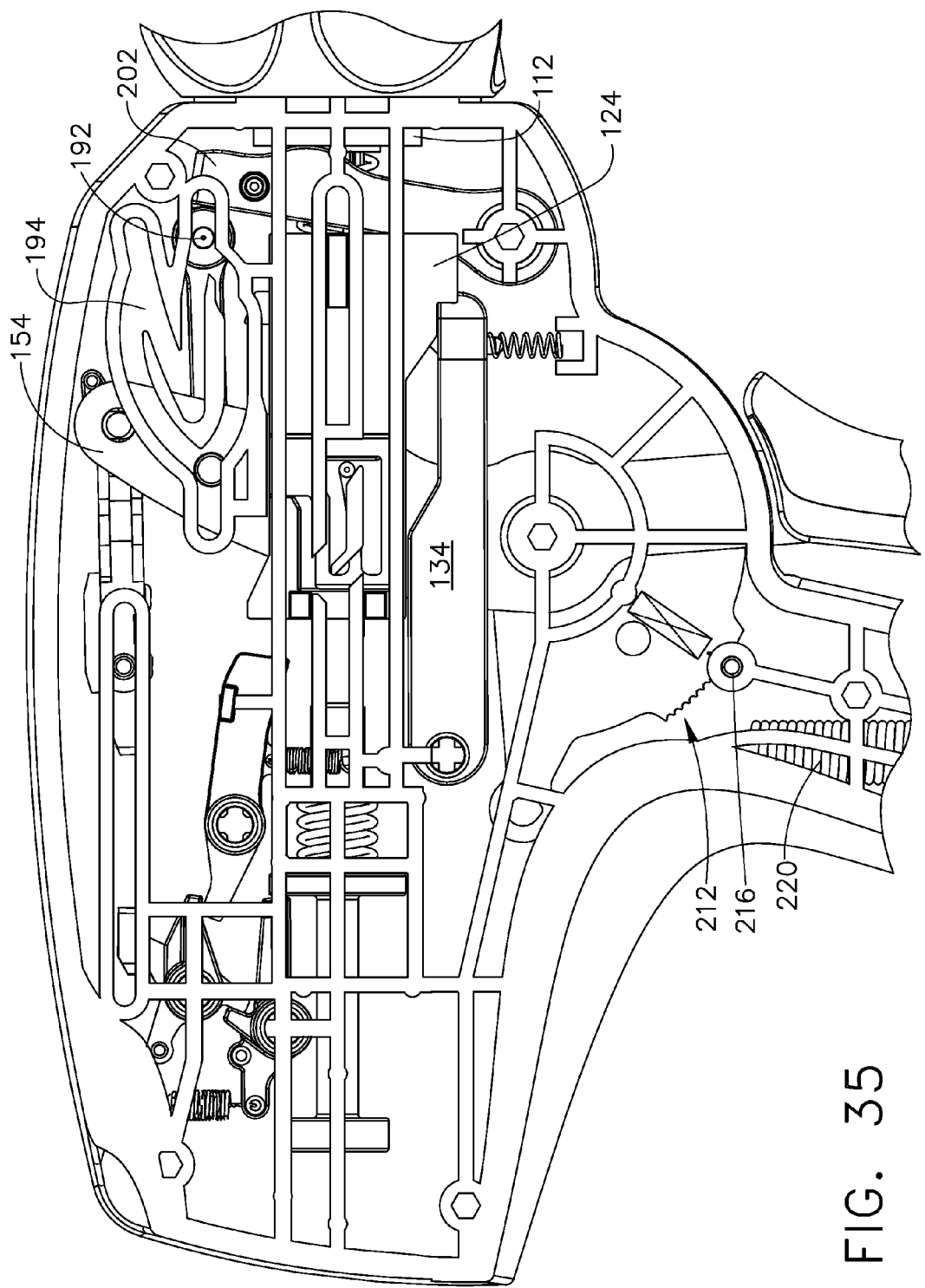
FIG. 35 is a right side view of the proximal end of the stapler with the outer cover removed, showing the same deployment condition as FIG. 33.

After the prongs 46 of the expanded staple 30 have been inserted at the desired tissue locations, the staple is formed through the tissue by again applying squeezing pressure to trigger grip 152. The pressure on grip 152 pivots actuator 16, causing transfer link 190 to advance distally within the third leg of transfer cam path 194. As link 190 advances distally, the link applies force against the former lever 202, which in turn pushes against former bushing 112, as shown in FIGS. 33 and 35. The force of transfer link 190 drives the bushing 112 forward, compressing former return spring 114. Former bushing 112 pushes housing 20 distally relative to the fixed staple deploying assembly, with slot 87 sliding past guide key 78 as the housing advances relative to the fixed staple guide 82. Housing 20 moves former 50 distally, drawing grooves at the distal end of the former against the expanded staple legs 34, 36. The expanded staple is held fixed relative to the moving former 50 by clamp 60 and anvil tines 56. The distal pushing force of former 50 against the expanded staple legs 34, 36 forces the legs to bend forward about the fixed anvil tines 56, closing the staple, as shown in FIG. 34.

In the finished, closed shape, the width of the staple is greater than the previous, undeployed width, due to the different bending points along the staple length. This change in staple width enables the staple to have a low profile during delivery and a larger profile when formed through tissue. As staple legs 34, 36 are bending forward, prongs 46 are drawn back inward, grabbing onto the tissue or material in the spread between the prongs. As prongs 46 move inward, staple ends 40, 42 traverse an arc through the tissue, drawing the tissue into the closing staple. As prongs 46 reach an inward, preferably overlapping position, in which the staple 30 passes through the gripped tissue, former 50 reaches its distal-most position. Inside handle 12, handle lockout pawl 216 advances over ratchet teeth 212, preventing distal movement of former 50 until the former is in a distal-most position, as shown in FIG. 35. At the distal-most position, lockout pawl 216 reaches release notch 214, enabling actuator 16 to pivot back open under the force of return spring 220.

Figure 38:
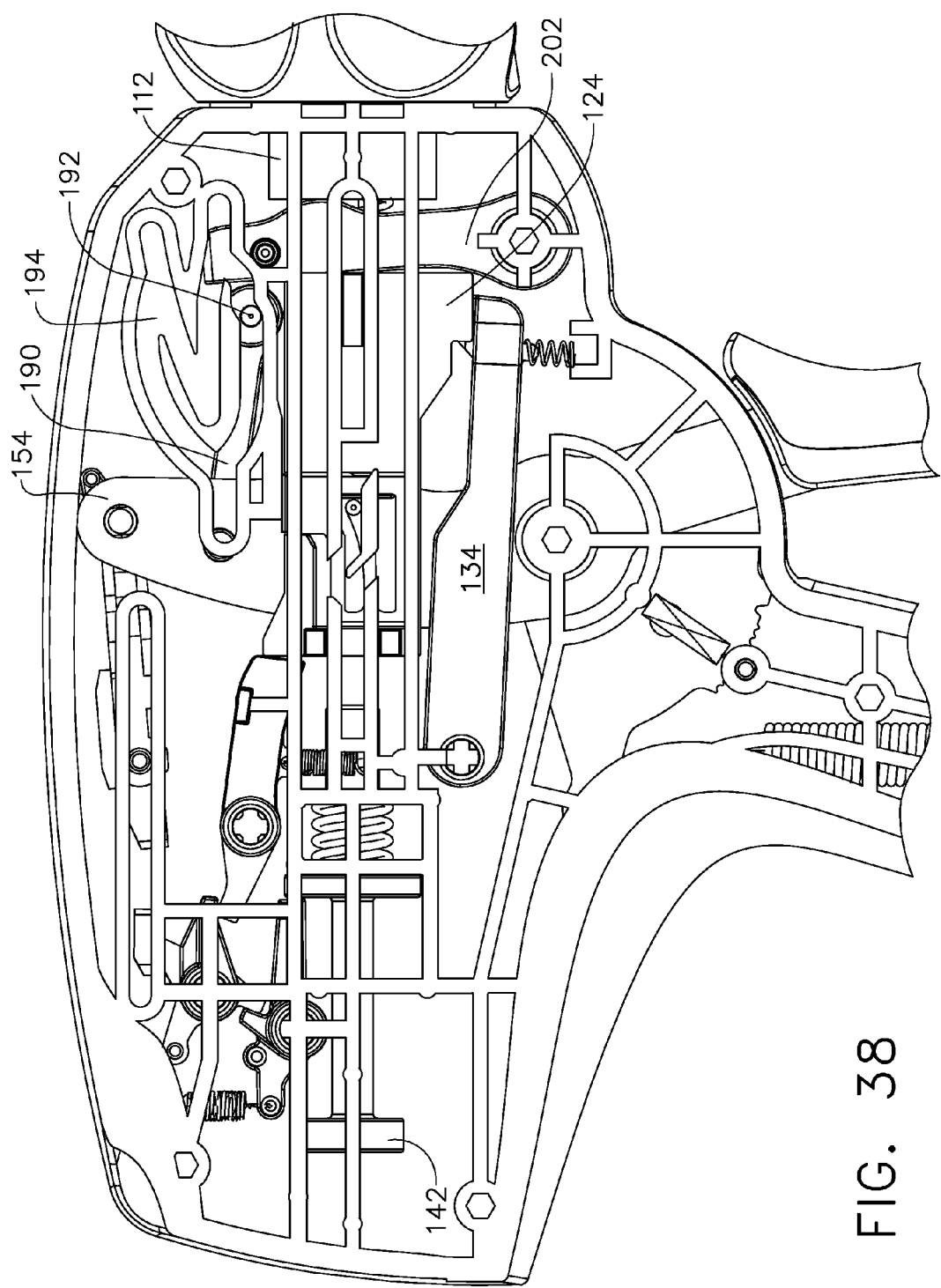
FIG. 38 is a right side view of the proximal end of the stapler with the outer cover removed, showing the same deployment condition as FIG. 36.

As actuator 16 pivots open, as shown in FIGS. 36 and 38, actuator lobes 154 rotate back, pulling transfer link 190 back proximally, and dropping link pin 192 from the third to the fourth leg of transfer cam path 194. As transfer link 190 moves proximally, the force against former lever 202 is removed, allowing the lever and former bushing 112 to retract proximally from the release of compression in former return spring 114. As former 50 retracts, key 78 moves to the distal end of housing slot 87, and former 50 is drawn away from the closed staple 30, as shown in FIG. 37, releasing the staple from the former. As transfer link 190 continues moving back proximally through the fourth leg of cam path 194, the link pushes against the distal angled face of clamp L-latch 134, as shown in FIG. 36. The contact with L-latch 134 pushes the latch down from clamp yoke 124, as shown in FIG. 38. Clamp yoke 124 then retracts back into contact with proximal clamp latch 180, pulling clamp 60 back proximally inside former 50. As clamp 60 retracts, control pin 80 rotates staple advancers 76 down into clamp extension trough 72. The staple advancers 76 retract back beneath the staple stack 70, leaving the stack in a distally indexed condition. Staple guide arms 83 hold the individual staples in stack 70 distally as the clamp extension retracts beneath the staples. As clamp 60 retracts proximally, the anvil arms retract back inward within the closed staple 30, releasing the pressure of anvil tines 56 against staple legs 34, 36. The formed staple 30 remains locked in the tissue (not shown), and held against anvil tines 56 outside the open stapler end 22. With the anvil arms retracted, staple 30 can be released from the stapler by maneuvering the anvil 52 away from the staple. As actuator 16 pivots fully open, transfer link pin 192 reaches the proximal end of the transfer cam path 190, resetting the transfer link back to the initial deployment position shown in FIGS. 12 and 14. Actuator 16 opens fully to the initial deployment position, and the stapler 10 resets back to the initial deployment condition, with the distal-most staple in stack 70 again staged between shoe side rails 88 and clamp 60 in preparation for the next deployment sequence.

If anvil tines 56 retract back inside former 50 before staple 30 is released, the anvil 52 can be pushed out distally by inserting a forceps or similar tool into the proximal handle opening 150. Through opening 150, the forceps can push against anvil release member 142 to drive anvil stop 140 distally. Release member 142 can be pushed until anvil stop 140 is again locked forward by anvil latch 184, to hold the anvil tines 56 outside the open end 22 of the stapler.

After the staple 30 is released from anvil 52, stapler 10 is preferably moved to a second targeted location along an intended fold line in a cavity wall or tissue apposition. Additional staples are preferably deployed along the cavity wall to extend the length of the fold. Additional details regarding GVR procedures and the use of a stapling device, such as the staple deploying device of the present invention, in a GVR procedure; as well as other surgical applications for the stapling device of the present invention, can be found in commonly assigned U.S. patent application Ser. No. 12/359,351, which was previously incorporated by reference into this application.

To complete the laparoscopic greater curvature plication (LGCP) procedure described in the previously referenced article by Brethauer et al. with this device, it is envisioned that this device should be able to fire at least forty staples without the need for reloading the device. It is also conceived that such a device may be used for other applications and would be able to fire at least twenty staples without the need for reloading the device. For LGCP it is conceived that an optimal procedure would comprise the following steps. The patient should be placed in the supine position. A five trocar port technique is utilized. In most cases, five 5-mm ports are placed. A Veress needle technique or Hassan technique can be utilized to establish pneumoperitoneum. A 5-mm trocar is placed above the umbilicus and slightly to the right of midline. The laparoscope is inserted and the abdomen is inspected. Trocars are then placed in the following locations under direct visualization: a 5-mm trocar in the right upper quadrant, a 5-mm trocar in the right upper quadrant below the 10-mm trocar at the auxiliary line, a 5-mm trocar below the xiphoid appendices, and a 5-mm trocar in the left upper quadrant. Percutaneous graspers and magnetically guided camera systems may be used to reduce the number of trocars used in this procedure. The greater curvature is then freed from its attachment points. The dissection starts at the distal body of the stomach along the greater curvature and continues proximally to the Angle of His. The left crus should be seen and the fundus mobilized off of the left crus. The dissection is then continued distally along the greater curvature to within 4-6 cm of the pylorus. Posterior gastric adhesions can be taken down as needed. Care should be taken to ensure that the dissection occurs approximately 0.5-1.0 cm from the greater curvature to avoid thermal damage to the gastric wall. The plication is ideally comprised of at least two rows of staples. To create the first row, an endoscope or bougie in place for sizing and the greater curvature is imbricated from the angle of His to within 4-6 cm of the pylorus. Approximately 10 staples should be used in this row with the spacing between staples kept at approximately 2-3 cm. The first staple is placed approximately 2 cm from the Angle of His. When creating plications, care must be taken not to obstruct at the EG junction and the angularis incisura as these are the two most common sites of obstruction. Intraoperative endoscopy, bougies with features, pressure based measurement systems, etc. may be used to aid in the sizing of the plication during its formation. To create the second row, the process is repeated starting near the Angle of His and extending the plication about the first row to the vicinity of the pylorus. As this second row is intended to be the final row, the spacing between staples should be no more than 1 cm. It is conceived that approximately 30 staples should be in this row for an average sized human stomach. A leak test with methylene blue can be performed or an insufflations test with the endoscope can be used to check for a leak.

Figure 39:
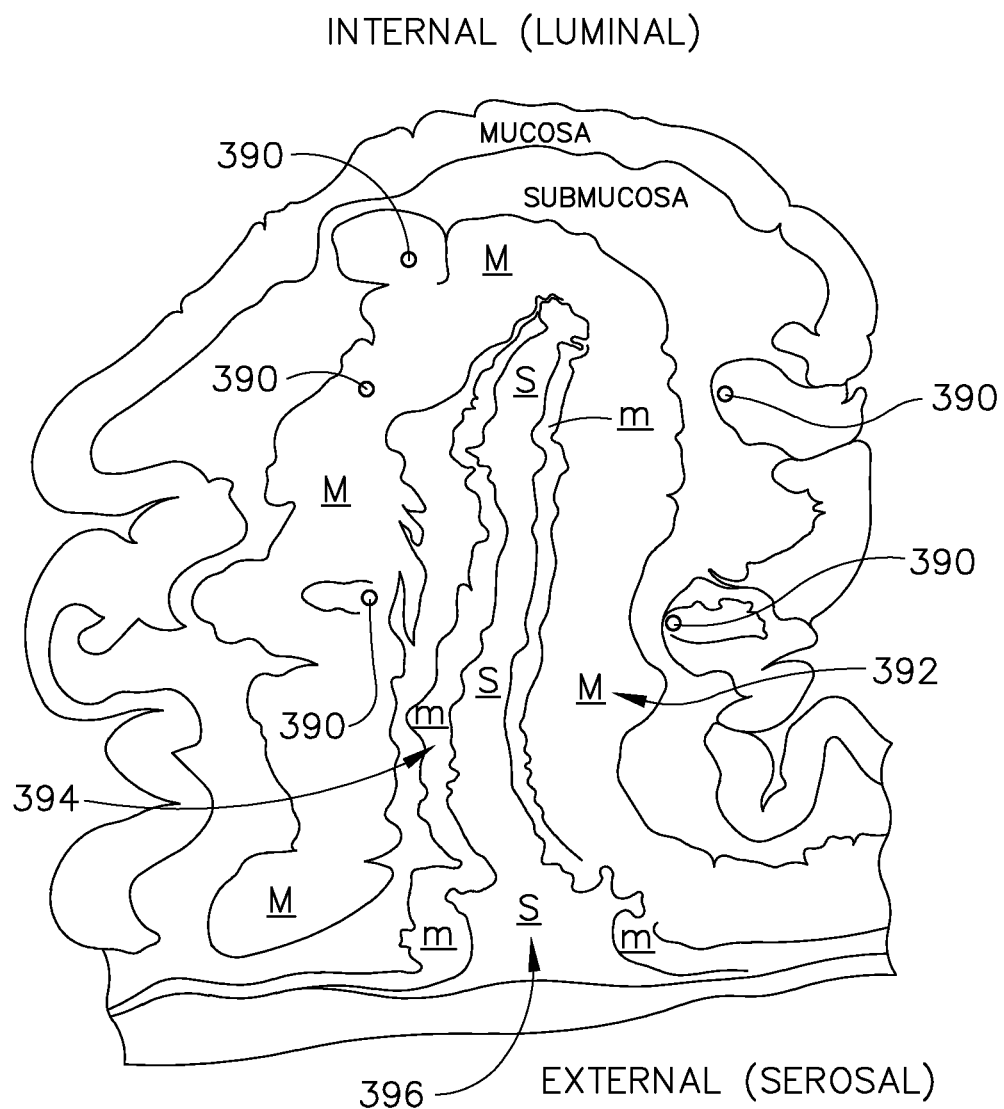
FIG. 39 is a photomicrograph at 8 weeks of a distal (pyloric) portion of a plication site from a canine model.
Figure 40:
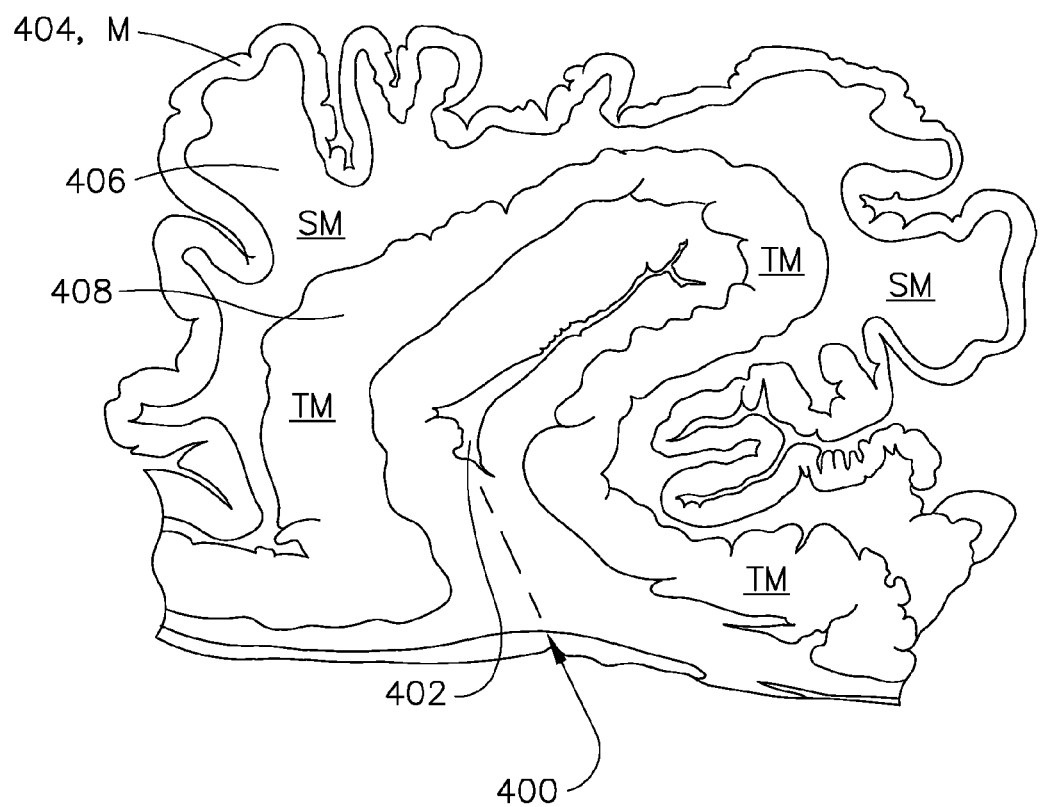
FIG. 40 is a histologic image of single row of suture at greater curvature. In regions of fold not containing fasteners, serosal surfaces did not bond.
Figure 41:
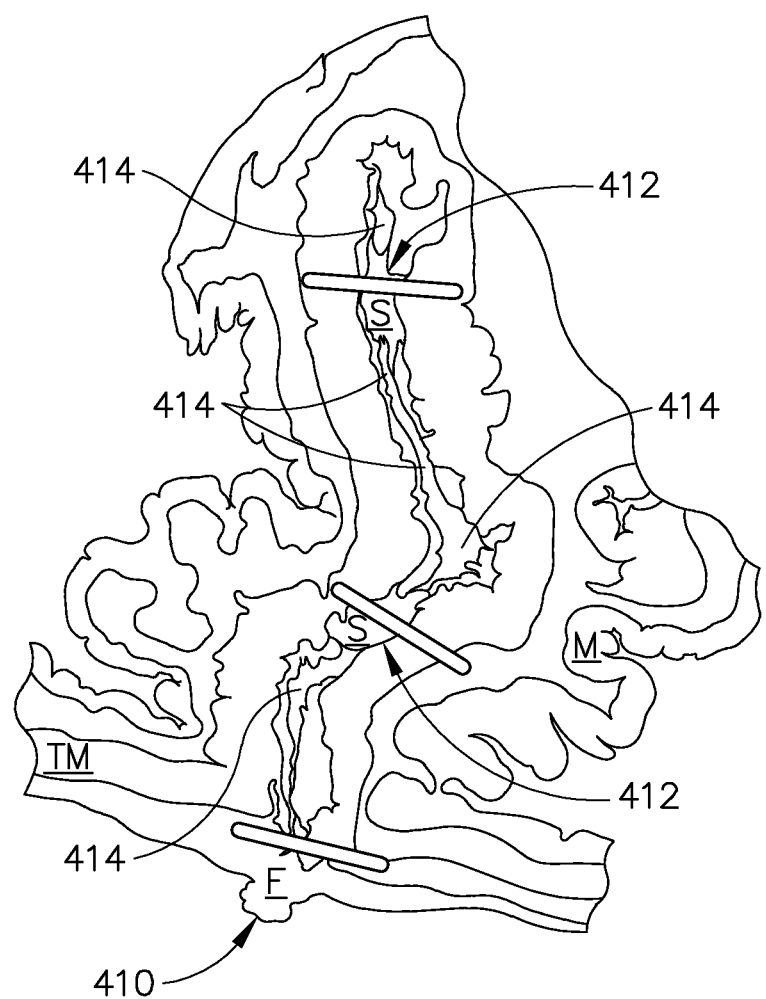
FIG. 41 is a photomicrograph at 8 weeks of a proximal (esophageal) portion of a plication site from a canine model.

Figures from the previously referenced article by Menchaca et al. disclose different fastener patterns for creating durable plications in a canine model. They present data on a range of patterns, fasteners, and surface pretreatments. They show two histology images showing the differences between plications created with sutures using different patterns. FIG. 39 shows a histologic image from Menchaca et al. wherein the plication was formed with multiple rows of suture resulting in a durable plication. In FIG. 39, arrows 390 point to spaces with suture. The internal tunica muscularis 392 is denoted by the region containing the letter 'M'. The external tunica muscularis 394 is denoted by the region containing the letter 'm'. The serosal surfaces have been replaced with a dense collagenous scar 396 denoted by the region containing the letter 'S'. FIG. 40 shows a second histologic image from Menchaca et al. In FIG. 40, fibrous healing 400 of the plication is evident on the exterior (serosal) surface of the stomach. The mucosa 404 is denoted by the region containing the letter 'M'. The submucosa 406 is denoted by the region containing the letters 'SM'. The tunica muscularis 408 is denoted by the region containing the letters 'TM'. In contrast to FIG. 39 serosal space 402 is present within the region of the fold. The plication in FIG. 40 was formed with a single row of suture in an interrupted pattern. They state that "Intermittent point failures in serosal apposition occurred in those dogs that had received only 1 row of fasteners; in regions of the fold not containing fasteners, the serosal surfaces had not bonded". FIG. 41 shows an unpublished histologic image from a similar study performed with the device described in this application. In FIG. 41 the histologic image shows the folded gastric wall is fused together by chronic inflammation/fibrosis 410 denoted by the region containing the letter 'F' at the base of the fold (base of the pre-existing serosa). In this study, three rows of staples were used to create a plication in a canine model. The inner rows had a coarse (2-3 cm) spacing as described above whereas the outermost row was comprised of staples having an approximately 1 cm spacing. As such, aside from the region of fibrosis 410 which corresponds to the outermost or final row of staples, there are two areas of serosal fusion 412 in the fold denoted by the regions containing the letter 'S'. Regions of the fold remained unbounded between rows resulting in free space 414, but no intermittent point failures were observed. Thus the pattern described above is uniquely more durable than that described in Menchaca et al. Further, that this durability was achieved with the presence of free space between the rows allows for easier reversal of this procedure as tissue dissection planes are easily identified. This is a significant advantage noted by potential patients of this procedure or any other bariatric surgical procedure. Applying an approximate spacing of 1 cm along a significant portion of the greater curvature of the stomach with a sutured pattern requires significant time and skill. The described device when used with the pattern described (e.g., at a minimum employing at least one row with approximately 1 cm spacing on the outermost row) provides unique and unforeseen advantages over existing technology. A durable plication can be created quickly and easily, without point failures, while resulting in the presence of free space facilitating easier reversal with standard laparoscopic techniques.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, ethylene oxide (EtO) gas, or high-energy electrons. The radiation kills bacteria on the instrument and in the container. The sterilized instrument can then be stored in the sterile container. The sealed container keeps the instrument sterile until it is opened in the medical facility.

In addition to reconditioning, stapler 10 of the present invention may also be reloaded with an additional stack of staples for use in multiple different surgical procedures. To reload the stapler, the distal end 94 of the staple housing is unscrewed from castle nut 100. Housing 20 is removed to expose the inner components of the staple deploying assembly. Staple guide 82 and clamp extension 64 are then separated and a new staple stack 70 laid in position between the two parts. After the stack of staples is loaded, the staple guide and clamp extension are repositioned on opposite planar surfaces of the stack. The staple housing 20 is then slid back over the staple deploying assembly and reattached at the proximal end to castle nut 100. Staple housing 20 can be adjusted via castle nut 100, as described above, to obtain the optimal staple housing length for opening and forming staples during deployment.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A fastener applying device comprising:
   a. a staple housing having a proximal end attached to a handle, a distal end and a longitudinal axis therebetween;
   b. at least one fastener within said housing;
   c. an anvil movable within said staple housing and being operable to individually convey fasteners through the staple housing distal end, said anvil having a proximal position and a distal position, wherein when in said distal position a distal end of said anvil extends distal to said distal end of said staple housing by a distance; and
   d. an adjustment nut connecting said staple housing to said handle, wherein rotation of said adjustment nut changes said distance.

* * * * *